US010113162B2

(12) United States Patent
Mathis et al.

(10) Patent No.: US 10,113,162 B2
(45) Date of Patent: Oct. 30, 2018

(54) MODIFYING SOYBEAN OIL COMPOSITION THROUGH TARGETED KNOCKOUT OF THE FAD2-1A/1B GENES

(71) Applicant: CELLECTIS, Paris (FR)

(72) Inventors: Luc Mathis, Le Kremlin Bicetre (FR); Daniel F. Voytas, Falcon Heights, MN (US); Feng Zhang, Plymouth, MN (US); William Haun, St. Paul, MN (US)

(73) Assignee: CELLECTIS, Paris (FR)

( * ) Notice: Subject to any disclaimer, the term of this patent is extended or adjusted under 35 U.S.C. 154(b) by 115 days.

(21) Appl. No.: 14/208,027

(22) Filed: Mar. 13, 2014

(65) Prior Publication Data

US 2014/0370558 A1 Dec. 18, 2014

Related U.S. Application Data

(60) Provisional application No. 61/790,655, filed on Mar. 15, 2013.

(51) Int. Cl.
*C12N 15/82* (2006.01)
*C12N 15/01* (2006.01)
*C12P 7/64* (2006.01)
*C12N 9/02* (2006.01)

(52) U.S. Cl.
CPC .......... *C12N 15/01* (2013.01); *C12N 9/0071* (2013.01); *C12N 15/8247* (2013.01); *C12P 7/6445* (2013.01); *C12Y 114/19006* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. |
| 4,683,195 A | 7/1987 | Mullis et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,959,317 A | 9/1990 | Sauer |
| 4,975,374 A | 12/1990 | Goodman et al. |
| 5,006,333 A | 4/1991 | Saifer et al. |
| 5,013,659 A | 5/1991 | Bedbrook et al. |
| 5,162,602 A | 11/1992 | Somers et al. |
| 5,204,253 A | 4/1993 | Sanford et al. |
| 5,276,268 A | 1/1994 | Strauch et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,501,967 A | 3/1996 | Offringa et al. |
| 5,538,880 A | 7/1996 | Lundquist et al. |
| 5,554,798 A | 9/1996 | Lundquist et al. |
| 5,561,236 A | 10/1996 | Leemans et al. |
| 5,591,616 A | 1/1997 | Hiei et al. |
| 5,767,366 A | 6/1998 | Sathasivan et al. |
| 5,792,640 A | 8/1998 | Chandrasegaran |
| 5,879,903 A | 3/1999 | Strauch et al. |
| 5,928,937 A | 7/1999 | Kakefuda et al. |
| 6,084,155 A | 7/2000 | Volrath et al. |
| 6,326,166 B1 | 12/2001 | Pomerantz et al. |
| 6,329,571 B1 | 12/2001 | Hiei |
| 6,368,227 B1 | 4/2002 | Olson |
| 6,451,732 B1 | 9/2002 | Beckett et al. |
| 6,451,735 B1 | 9/2002 | Ottaway et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,001,768 B2 | 2/2006 | Wolffe |
| 7,013,219 B2 | 3/2006 | Case et al. |
| 7,067,722 B2 | 6/2006 | Fillatti |
| 7,070,934 B2 | 7/2006 | Cox, III et al. |
| 7,163,824 B2 | 1/2007 | Cox, III et al. |
| 7,189,691 B2 | 3/2007 | Hemenway |
| 7,220,719 B2 | 5/2007 | Case et al. |
| 7,262,054 B2 | 8/2007 | Jamieson et al. |
| 7,273,923 B2 | 9/2007 | Jamieson et al. |
| 7,285,416 B2 | 10/2007 | Choo et al. |
| 7,361,635 B2 | 4/2008 | Miller et al. |
| 7,521,241 B2 | 4/2009 | Choo et al. |
| 7,842,489 B2 | 11/2010 | Arnould et al. |
| 8,420,782 B2 | 4/2013 | Bonas et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,586,363 B2 | 11/2013 | Voytas et al. |
| 8,697,853 B2 | 4/2014 | Voytas et al. |

(Continued)

FOREIGN PATENT DOCUMENTS

| | | |
|---|---|---|
| CN | 1724669 | 1/2006 |
| EP | 0 242 246 | 10/1987 |
| EP | 2 206 723 | 7/2010 |
| EP | 2 392 208 | 12/2011 |

(Continued)

OTHER PUBLICATIONS

Hill et al (Functional analysis of conserved histidines in ADP-glucose pyrophosphorylase from *Escherichia coli*. Biochem. Biophys. Res. Com
Guo et al (Protein tolerance to random amino acid change, Proc. Natl. Acad. Sci. USA 101:9205-9210, 2004).*
Baker (Gene-editing nucleases. Nature methods. 9: 23-27, Jan. 2012).*
Garba et al (Review on Fatty Acid Desaturases and their Roles in Temperature Acclimatisation. J. Applied Sci., 17 (6): 282-295, 2017).* :573-577, 1998).*

(Continued)

*Primary Examiner* — Medina A Ibrahim
*Assistant Examiner* — Wayne Zhong
(74) *Attorney, Agent, or Firm* — Fish & Richardson P.C.

(57) ABSTRACT

Materials and methods are provided for making soybean varieties that have altered oil composition as a result of mutations in the FAD2-1A and FAD2-1B genes.

13 Claims, 6 Drawing Sheets

Specification includes a Sequence Listing.

(56) References Cited

U.S. PATENT DOCUMENTS

| | | | |
|---|---|---|---|
| 9,035,129 | B2 | 5/2015 | Bilyeu et al. |
| 9,198,365 | B2 | 12/2015 | Bilyeu et al. |
| 2001/0016956 | A1 | 8/2001 | Ward et al. |
| 2005/0064474 | A1 | 3/2005 | Umov et al. |
| 2007/0141038 | A1 | 6/2007 | Choulika et al. |
| 2009/0060921 | A1 | 3/2009 | Dickey et al. |
| 2009/0133158 | A1 | 5/2009 | Lahaye et al. |
| 2009/0271881 | A1 | 10/2009 | Arnould et al. |
| 2009/0305402 | A1 | 12/2009 | Liljedahl et al. |
| 2010/0132069 | A1 | 5/2010 | Lahaye et al. |
| 2010/0154081 | A1 | 6/2010 | Weterings et al. |
| 2011/0041195 | A1 | 2/2011 | Doyon |
| 2011/0129898 | A1 | 6/2011 | Doyon et al. |
| 2011/0136895 | A1 | 6/2011 | Gregory et al. |
| 2011/0145940 | A1 | 6/2011 | Voytas et al. |
| 2011/0158957 | A1 | 6/2011 | Bonini et al. |
| 2011/0167521 | A1 | 7/2011 | DeKelver et al. |
| 2011/0201055 | A1 | 8/2011 | Doyon et al. |
| 2011/0201118 | A1 | 8/2011 | Yang et al. |
| 2011/0203012 | A1 | 8/2011 | Dotson et al. |
| 2011/0207221 | A1 | 8/2011 | Cost et al. |
| 2011/0239315 | A1 | 9/2011 | Bonas et al. |
| 2011/0247089 | A1 | 10/2011 | Doyon |
| 2011/0265198 | A1 | 10/2011 | Gregory et al. |
| 2011/0269234 | A1 | 11/2011 | Doyon et al. |
| 2011/0287545 | A1 | 11/2011 | Cost et al. |
| 2011/0301073 | A1 | 12/2011 | Gregory et al. |
| 2012/0102587 | A1* | 4/2012 | Anai ............ A01H 1/04 800/264 |
| 2012/0110685 | A1 | 5/2012 | Bonas et al. |
| 2012/0122205 | A1 | 5/2012 | Bonas et al. |
| 2012/0178131 | A1 | 7/2012 | Voytas et al. |
| 2012/0178169 | A1 | 7/2012 | Voytas et al. |
| 2012/0214228 | A1 | 8/2012 | Voytas et al. |
| 2012/0246764 | A1 | 9/2012 | Hlubek et al. |
| 2012/0284877 | A1 | 11/2012 | Hlubek et al. |
| 2012/0324603 | A1 | 12/2012 | Hlubek et al. |
| 2013/0122581 | A1 | 5/2013 | Voytas et al. |
| 2014/0090116 | A1 | 3/2014 | Ainley et al. |

FOREIGN PATENT DOCUMENTS

| | | | |
|---|---|---|---|
| EP | 2 562 260 | 2/2013 | |
| JP | WO 2010150901 A1 * | 12/2010 | ............ A01H 1/04 |
| WO | WO 1994/18313 | 8/1994 | |
| WO | WO 1995/09233 | 4/1995 | |
| WO | WO 2004/067736 | 8/2004 | |
| WO | WO 2004067736 A2 * | 8/2004 | ......... A01K 67/0275 |
| WO | WO 2007/060495 | 5/2007 | |
| WO | WO 2008/141806 | 11/2008 | |
| WO | WO 2009/095793 | 8/2009 | |
| WO | WO 2010/079430 | 7/2010 | |
| WO | WO 2010/091018 | 8/2010 | |
| WO | WO 2010/145846 | 12/2010 | |
| WO | WO 2011/005998 | 1/2011 | |
| WO | WO 2011/017293 | 2/2011 | |
| WO | WO 2011/019385 | 2/2011 | |
| WO | WO 2011/049627 | 4/2011 | |
| WO | WO 2011/072246 | 6/2011 | |
| WO | WO 2011/100058 | 8/2011 | |
| WO | WO 2011/117249 | 9/2011 | |
| WO | WO 2011/146121 | 11/2011 | |
| WO | WO 2011/154393 | 12/2011 | |
| WO | WO 2012/106105 | 8/2012 | |
| WO | WO 2013/050155 | 4/2013 | |
| WO | WO 2014/039692 | 3/2014 | |
| WO | WO 2014/039702 | 3/2014 | |

OTHER PUBLICATIONS

Cermak et al (Efficient design and assembly of custom TALEN and other TAL effector-based constructs for DNA targeting. Nucleic Acids Research, 1-11, 2011).*

Pham et al (Mutant alleles of FAD2-1A and FAD2-1B combine to produce soybeans with the high oleic acid seed oil trait. BMC Plant Biology, 10:195, p. 1-13, 2010).*

International Search Report and Written Opinion in International Application No. PCT/IB2014/059752, dated Jul. 29, 2014, 16 pages.

Pham et al., "A novel FAD2-1 allele in a soybean plant introduction offers an alternate means to produce soybean seed oil with 85% oleic acid content," Theoretical and Applied Genetics, Int J Plant Breeding Res, 123(5):793-802 (Jun. 2011).

U.S. Appl. No. 61/255,043, Bonas et al.

"TAL effector nucleases," Nature Reprint Collection [online]. Oct. 2011, [retrieved on Mar. 14, 2012]. Retrieved from the Internet: URL <http://www.nature.com/nbt/collections/talen/index.html>, 32 pages, Marshall (ed.).

Alam and Sittman, "Characterization of the cytotoxic effect of a chimeric restriction enzyme, H1°-FokI," Gene Ther Mol Biol, 10:147-160, 2006.

Alam, "Characterization of the cytotoxic effect of a novel chimeric restriction nuclease, H1°-FokI, in mouse fibroblast cells: Implications for chromatin mapping and gene therapy studies," Ph.D. Thesis, The University of Mississippi Medical Center, 223 pages, 2006.

Al-Saadi et al., "All five host-range variants of Xanthomonas citri carry one pthA homolog with 17.5 repeats that determines pathogenicity on citrus, but none determine host-range variation," Mol Plant Microbe Interact, 20(8): 934-943, 2007.

Antony et al., "Rice xa13 recessive resistance to bacterial blight is defeated by induction of the disease susceptibility gene Os-11N3," Plant Cell, 22(11):3864-3876, 2010.

Antony, "Molecular basis of avrXa7 mediated virulence in bacterial blight of rice," [abstract of dissertation] Kansas State University, 99 pages, 2010.

Arimondo et al., "Exploring the cellular activity of camptothecin-triple-helix-forming oligonucleotide conjugates," Mol Cell Biol, 26:324-333, 2006.

Athinuwat et al., "Xanthomonas axonopodis pv. glycines soybean cultivar virulence specificity is determined by avrBs3 homolog avrXgl," Phytopathology, 99(8):996-1004, 2009.

Bai et al., "Xanthomonas oryzae pv. oryzae avirulence genes contribute differently and specifically to pathogen aggressiveness," Mol Plant Microbe Interact, 13(12):1322-1329, 2000.

Baker, "Gene-editing nucleases," Nature Methods, 9:23-26, 2012.

Ballvora et al., "Genetic mapping and functional analysis of the tomato Bs4 locus governing recognition of the Xanthomonas campestris pv. vesicatoria AvrBs4 protein," Mol Plant Microbe Interact, 14(5):629-638, 2001.

Belahj et al., "Plant genome editing made easy: targeted mutagenesis in model and crop plants using the CRISPR/Cas system," Plant Methods, 9:39, 2013.

Beretta et al., "Tethering a type IB topoisomerase to a DNA site by enzyme fusion to a heterologous site-selective DNA-binding protein domain," Cancer Res, 59:3689-3697, 1999.

Bethke and Busse, "Validation of a simple, colorimetric, microplate assay using amplex red for the determination of glucose and sucrose in potato tubers and other vegetables," Am. J. Pot Res., 85:414-421, 2008.

Beuselinck et al., "An Assessment of Phenotype Selection for Linolenic Acid Using Genetic Markers," Crop Sci, 47:747-750, 2006.

Bhaskar et al., "Suppression of the vacuolar invertase gene prevents cold-induced sweetening in potato,"Plant Physiol., 154(2):939-948, 2010.

Bibikova et al., "Enhancing gene targeting with designed zinc finger nucleases," Science, 300(5620):764, 2003.

Bibikova et al., "Stimulation of homologous recombination through targeted cleavage by chimeric nucleases," Mol Cell Biol, 21(1): 289-297, 2001.

Bitinaite et al., "FokI dimerization is required for DNA cleavage," Proc Natl Acad Sci USA, 95:10570-10575, 1998.

Boch and Bonas. "Xanthomonas AvrBs3 family-type III effectors: discovery and function." Annu Rev Phytopathol, 48, 419-436, 2010.

(56) References Cited

OTHER PUBLICATIONS

Boch et al., "Breaking the code of DNA binding specificity of TAL-type III effectors," Science, 326:1509-1512, 2009.
Boch et al., "Molecular characterization of three AvrBs3-like effectors from the Arabidopsis pathogen Xanthomonas campestris pv. armoraciae," (abstract), XIV International Congress on Molecular Plant-Microbe Interactions, Quebec City, Canada, Jul. 19-23, 2009, 2 pages.
Bogdanove et al., "TAL effectors: Customizable Proteins for DNA Targeting," Science, 333: 1843-1846, 2011.
Bogdanove et al., "TAL effectors: finding plant genes for disease and defense," Curr Opin Plant Biol, 13:394-401, 2010.
Boller and He, "Innate immunity in plants: an arms race between pattern recognition receptors in plants and effectors in microbial pathogens," Science, 324:742-744, 2009.
Bonas et al., "Resistance in tomato to Xanthomonas campestris pv vesicatoria is determined by alleles of the pepper-specific avirulence gene avrBs3," Mol Gen Genet, 328: 261-269, 1993.
Bonas et al., "Genetic and structural characterization of the avirulence gene avrBs3 from Xanthomonas campestris pv. Vesicatoria," Mol Gen Genet, 218:127-136, 1989.
Bonas et al., "How the bacterial plant pathogen Xanthomonas campestris pv. vesicatoria conquers the host," Mol Plant Pathol, 1(1):73-76, 2000.
Bonas et al., "Resistance in tomato to Xanthomonas campestris pv vesicatoria is determined by alleles of the pepper-specific avirulence gene avrBs3," Mol Gen Genet, 238(1-2):261-269, 1993.
Bonas, "How Xanthomonas manipulates the plant cell," (abstract), XIV International Congress on Molecular Plant-Microbe Interactions, Quebec City, Canada, Jul. 19-23, 2009, 2 pages.
Borevitz et al., "Activation tagging identifies a conserved MYB regulator of phenylpropanoid biosynthesis," Plant Cell, 12:2383-2394, 2000.
Busk, "Regulatory elements in vivo in the promoter of the abscisic acid responsive gene rab17 from maize," Plant J, 11:1285-1295, 1997.
Büttner and Bonas, "Getting across—bacterial type III effector proteins on their way to the plant cell," EMBO J, 2002, 21(20):5313-5322, 2002.
Büttner et al., "Functional analysis of HrpF, a putative type III translocon protein from Xanthomonas campestris pv. vesicatoria," J Bacteriol, 184(9):2389-2398, 2002.
Büttner et al., "HpaB from Xanthomonas campestris pv. vesicatoria acts as an exit control protein in type III-dependent protein secretion," Mol Microbiol, 54(3):755-768, 2004.
Büttner et al., "Targeting of two effector protein classes to the type III secretion system by a HpaC- and HpaB-dependent protein complex from Xanthomonas campestris pv. vesicatoria," Mol Microbiol, 59(2):513-527, 2006.
Canteros et al., "A gene from Xanthomonas campestris pv. vesicatoria that determines avirulence in tomato is related to avrBs3," Mol Plant Microbe Interact, 4(6):628-632, 1991.
Carlson et al., "Targeting DNA With Fingers and TALENs," Mol Ther Nucl Acids, 1:e3, doi:10.1038/mtna.2011.5, 4 pages, 2012.
Cathomen et al., "Zinc-finger nucleases: the next generation emerges," Mol Ther, 16(7):1200-1207, 2008.
Cavalier et al., "Disrupting Two Arabidopsis thaliana Xylosyltransferase Genes Results in Plant Deficient in Xyloglucan, a Major Primary Cell Wall Component," The Plant Cell, 20:1519-1537, 2008.
Cermak et al., "Efficient design and assembly of custom TALEN and other TAL effector-based constructs for DNA targeting," Nucleic Acids Res, 39:e82, 2011.
Cermak et al., Poster and Abstract—"Engineered TAL effector nucleases: new tools for genome editing," Northwest Genome Engineering Consortium Workshop on Genome Engineering, 3 pages, 2010.
Chevalier et al., "Design, activity, and structure of a highly specific artificial endonuclease," Mol Cell, 10(4):895-905, 2002.
Choo et al., "In vivo repression by a site-specific DNA-binding protein designed against an oncogenic sequences," Nature, 372(6507):642-645, 1994.
Choulika et al., "Induction of homologous recombination in mammalian chromosomes by using the I-SceI system of Saccharomyces cerevisiae," Mol Cell Biol, 15(4):1968-1973, 1995.
Christian et al., "Targeting DNA double-strand breaks with TAL effector nucleases," Genetics, 186:757-761, 2010.
Christian et al., Poster and Abstract—"Fusions of TAL effectors to the FokI endonuclease confer site specificity in DNA cleavage," IAPB 12th World Congress and In Vitro Biology Meeting, 4 pages, 2010.
Cole et al., "The Jpred 3 secondary structure prediction server," Nucl Acids Res, 36:W197-W201, 2008.
Cornelis, "The type III secretion injectisome," Nat Rev Microbiol, 4:811-825, 2006.
Curtin et al., "Targeted mutagenesis of duplicated genes in soybean with zinc-finger nucleases," Plant Physiology, 156(2):466-473, 2011.
De Feyter et al., "Gene-for genes interactions between cotton R genes and Xanthomonas campestris pv. malvacearum avr genes," Mol Plant Microbe Interact, 6(2):225-237, 1993.
Defrancesco, "Move over ZFNs," Nat Biotechnol, 29: 681-684, 2011.
Desjarlais and Berg, "Toward rules relating zinc finger protein sequences and DNA binding site preferences," Proc Natl Acad Sci USA, 89:7345-7349, 1992.
Domingues et al., "The Xanthomonas citri effector protein PthA interacts with citrus proteins involved in nuclear transport, protein folding and ubiquitination associated with DNA repair," Mol Plant Pathol, 11(5):663-675, DOI: 10.1111/J.1364-3703.2010.00636.X, 13 pages, 2010.
Doyle et al., "TAL Effector-Nucleotide Targeter (TALE-NT) 2.0: tools for TAL effector design and target prediction," Nucleic Acids Res, 40:W117-122, 2012.
Draffehn et al., "Natural diversity of potato (Solanum tuberosum) invertases," BMC Plant Biol., 10:271, 15 pages, 2010.
Durai et al., "Zinc finger nucleases: custom-designed molecular scissors for genome engineering of plant and mammalian cells," Nucl Acids Res, 33(1): 5978-5990, 2005.
Eisenschmidt et al., "Developing a programmed restriction endonuclease for highly specific DNA cleavage," Nucl Acids Res, 33:7039-7047, 2005.
Engler et al. "A One Pot, One Step, Precision Cloning Method with High Throughput Capability," PLoS One, 3: e3647, 7 pages, 2008.
Engler et al., "Golden Gate Shuffling: A One-Pot DNA Shuffling Method Based on Type IIs Restriction Enzymes," PLoS One, 4:e5553, 9 pages, 2009.
Fajardo-Sanchez et al., "Computer design of obligate heterodimer meganucleases allows efficient cutting of custom DNA sequences," Nucl Acids Res, 36(7):2163-2173, 2008.
Foley et al., "Rapid Mutation of Endogenous Zebrafish Genes Using Zinc Finger Nucleases Made by Oligomerized Pool ENgineering (OPEN)," PLoS One, 13 pages, 4:e4348, 2009.
Fonfara et al., "Creating highly specific nucleases by fusion of active restriction endonucleases and catalytically inactive homing endonucleases," Nucl Acids Res, 40(2):847-860, 2011.
Fujikawa et al., "Suppression of defense response in plants by the avrBs3/pthA gene family of Xanthomonas spp," Mol Plant Microbe Interact, 19(3):342-349, 2006.
Gabriel et al.," An unbiased genome-wide analysis of zinc-finger nuclease specificity," Nat Biotechnol, 29:816-823, 2011.
Geißler et al., "Transcriptional activators of human genes with programmable DNA-specificity," PLoS One, 6(5):e19509, May 2011.
GenBank Accession No. AAT46122, Nov. 12, 2004, 2 pages.
GenBank Accession No. ACD58243, May 19, 2008, 2 pages.
GenBank Accession No. AY986492, Jun. 24, 2005, 2 pages.
GenBank Accession No. CP000967, GI: 188518722, May 19, 2008, 606 pages.
GenBank Accession No. J04623, Apr. 26, 1993, 2 pages.
GenBank Accession No. M28828, Apr. 26, 1993, 3 pages.
GenBank Accession No. P14727, Jun. 28, 2011, 3 pages.

(56) References Cited

OTHER PUBLICATIONS

GenBank Accession No. X16130, Oct. 15, 2007, 3 pages.
Göhre and Robatzek, "Breaking the barriers: microbial effector molecules subvert plant immunity," Ann Rev Phytopathol, 46:189-215, 2008.
Gonchar et al., PspXI, a novel restriction endonuclease that recognizes the unusual DNA sequence 5'-VC↓TCGAGB-3', Bulletin of biotechnology and physico-chemical biology, 1(1):18-24, 2005, Translation by Ovchinnikov, "Science sibenzyme.com" [online], [retrieved on Aug. 11, 2011]. Retrieved from the Internet: URL: <http://science.sibenzyme.com/article8_article_3_1.phtml>, 4 pages.
Gonzalez et al., "Molecular and pathotypic characterization of new Xanthomonas oryzae strains from West Africa," Mol Plant Microbe Interact, 20(5):534-546, 2007.
Govindarajulu et al., "Evaluation of constitutive viral promoters in transgenic soybean roots and nodules," *Mol. Plant Microbe Interact*, 21:1027-1035, 2008.
Greiner et al., "Ectopic expression of a tobacco invertase inhibitor homolog prevents cold-induced sweetening of potato tubers," *Nature Biotechnology*, 17(7):708-711, 1999.
Greisman and Pabo, "A general strategy for selecting high-affinity zinc finger proteins for diverse DNA target sites," Science, 275(5300):657-661, 1997.
Gu et al., "R gene expression induced by a type-III effector triggers disease resistance in rice," Nature, 435:1122-1125, 2005.
Gu et al., "Transcription activator-like type III effector AvrXa27 depends on OsTFIIAgamma5 for the activation of Xa27 transcription in rice that triggers disease resistance to Xanthomonas oryzae pv. oryzae," Mol Plant Pathol, 10(6):829-835, 2009.
Guan et al., "Heritable endogenous gene regulation in plants with designed polydactyl zinc finger transcription factors," Proc Natl Acad Sci USA, 99(20):13296-13301, 2002.
Gürlebeck et al., "Dimerization of the bacterial effector protein AvrBs3 in the plant cell cytoplasm prior to nuclear import," Plant J, 42:175-187, 2005.
Gürlebeck et al., "Type III effector proteins from the plant pathogen Xanthomonas and their role in the interaction with the host plant," J Plant Physiol, 163(3):233-255, 2006 (Epub 2005).
Gürlebeck et al., "Visualization of novel virulence activities of the Xanthomonas type III effectors AvrBsl, AvrBs3, and AvrBs4," Mol Plant Pathol, 10(2):175-188, 2009.
Haber, "In vivo biochemistry: Physical monitoring of recombination induced by site-specific endonucleases," Bioessays, 17:609-620, 1995.
Haberlach et al., "Isolation, culture and regeneration of protoplasts from potato and several related Solanum species," *Plant Science*, 39:67-74, 1985.
Hahn et al., "New mechanistic insights into the virulence activity of the Xanthomonas type III effector AvrBs3," (abstract), XIV International Congress on Molecular Plant-Microbe Interactions, Quebec City, Canada, Jul. 19-23, 2009, 2 pages.
Halford et al., "The reaction mechanism of FokI excludes the possibility of targeting zinc finger nucleases to unique DNA sites," Biochem Soc Trans, 39:584-588, 2011.
Handel et al., "Expanding or restricting the target site repertoire of zinc-finger nucleases: the inter-domain linker as a major determinant of target site selectivity," Mol Ther, 17:104-111, 2009.
Haun et al., "Improved soybean oil quality by targeted mutagenesis of fatty acid desaturase 2 gene family," *Plant Biotechnology Journal*, 1-7, 2014.
Herbers et al., "Race-specificity of plant resistance to bacterial spot disease determined by repetitive motifs in a bacterial avirulence protein," Nature, 356:172-174, 1992.
Heuer et al., "Repeat domain diversity of avrBs3-like genes in Ralstonia solanacearum strains and association with host preferences in the field," Appl Environ Microbiol, 73(13):4379-4384, 2007.
Hockemeyer et al., "Genetic engineering of human pluripotent cells using TALE nucleases," Nat Biotechnol, 29(8):731-734, 2011.
Hopkins et al., "Identification of a family of avirulence genes from Xanthomonas oryzae pv. oryzae," Mol Plant Microbe Interact, 5(6):451-459, 1992.
Hu et al., "A virulence gene and insertion element-based RFLP as well as RAPD markers reveal high levels of genomic polymorphism in the rice pathogen Xanthomonas oryzae pv. oryzae," Syst Appl Microbiol, 30:587-600, 2007.
Huang et al., "Heritable gene targeting in zebrafish using customized TALENs," Nat Biotechnol, 29(8):699-700, 2011.
Hummel et al., "Rice gene activation by transcription activator-like effectors of Xanthomonas oryzae pvs. oryzae and oryzicola," poster presentation, and "A cipher-like mechanism governs TAL effector-DNA recognition," poster #13-517, XIV International Congress on Molecular Plant-Microbe Interactions, Quebec City, Canada, 3 pages, Jul. 19-23, 2009.
Hurt et al., "Highly specific zinc finger proteins obtained by directed domain shuffling and cell-based selection," Proc Natl Acad Sci USA, 100(21):12271-12276, 2003.
Isalan et al., "A rapid, generally applicable method to engineer zinc fingers illustrated by targeting the HIV-1 promoter," Nat Biotechnol, 19(7):656-660, 2001.
Jackel et al., "Protein design by directed devolution," Annu Rev Biophys, 37:155-173, 2008.
Jones and Dangl, "The plant immune system," Nature, 444:323-329, 2006.
Jordan et al., "Physical delimitation of the pepper Bs3 resistance gene specifying recognition of the AvrBs3 protein from Xanthomonas campestris pv. vesicatoria," Theor Appl Genet, 113(5):895-905, 2006.
Kay and Bonas, "How Xanthomonas type III effectors manipulate the host plant," Curr Opin Microbiol, 12:37-43, 2009.
Kay et al., "A bacterial effector acts as a plant transcription factor and induces a cell size regulator," *Science*, 318:648-651, 2007.
Kay et al., "Characterization of AvrBs3-like effectors from a Brassicaceae pathogen reveals virulence and avirulence activities and a protein with a novel repeat architecture," Mol Plant Microbe Interact, 18(8):838-848, 2005.
Kay et al., "Detailed analysis of the DNA recognition motifs of the Xanthomonas type III effectors AvrBs3 and AvrBs3deltarep16," Plant J, 59(6):859-871, 2009.
Kay et al., "Bacterial Effector Acts as a Plant Transcription Factor and Induces a Cell Size Regulator," Science, 318(5850):648-651, 2007.
Keshavarzi et al., "Basal defenses induced in pepper by lipopolysaccharides are suppressed by Xanthomonas campestris pv. vesicatoria," Mol Plant Microbe Interact, 17(7):805-815, 2004.
Kim and Chandrasegaran, "Chimeric restriction endonuclease," Proc Natl Acad Sci USA, 91(3):883-887, 1994.
Kim et al., "Comparative analysis of three indigenous plasmids from Xanthomonas axonopodis pv. glycines," Plasmid, 56(2):79-87, 2006.
Kim et al., "Construction of a Z-DNA-specific restriction endonuclease," Proc Natl Acad Sci USA, 94(24):12875-12879, 1997.
Kim et al., "Hybrid restriction enzymes: zinc finger fusions to FokI cleavage," Proc Natl Acad Sci USA, 93:1156-1160, 1996.
Kim et al., "Site-specific cleavage of DNA-RNA hybrids by zinc finger/FokI cleavage domain fusions," Gene, 203(1):43-49, 1997.
Kim et al., "Targeted genome editing in human cells with zinc finger nucleases constructed via modular assembly," *Genome Res*, 19:1279-1288, 2009.
Knoop et al., "Expression of avirulence gene avrBs3 from Xanthomonas campestris pv. vesicatoria is not under the control of hrp genes and is independent of plant factors," J Bacteriol, 173(22):7142-7150, 1991.
Lahaye and Bonas, "Molecular secrets of bacterial type III effector proteins," Trends Plant Sci, 6(10):479-485, 2001.
Ledford, "Plant genes get fine tailoring," Nature News [online], Apr. 29, 2009 [retrieved on May 21, 2009]. Retrieved from the Internet: <URL: http://www.nature.com/news/2009/090429/full/news.2009.415.html>, 3 pages.
Lee et al., "Environmental Effects on Oleic Acid in Soybean Seed Oil of Plant Introductions with Elevated Oleic Concentration," *Crop Science*, 49:1762-1768, 2009).

(56) References Cited

OTHER PUBLICATIONS

Li et al., "Functional domains in FokI restriction endonuclease," Proc Natl Acad Sci USA, 89(10):4275-4279, 1992.
Li et al., "Modularly assembled designed TAL effector nucleases for targeted gene knockout and gene replacement in eukaryotes," Nucl Acids Res, 39:6315-6325, 2011.
Li et al., "TAL nucleases (TALNs): hybrid proteins composed of TAL effectors and FokI DNA-cleavage domain," Nucleic Acids Research, 39(1):359-372, 2010.
Liang et al., "Cloning and characterization of a novel avirulence gene (arp3) from Xanthomonas oryzae pv. oryzae," DNA Seq, 15(2):110-117, 2004.
Liu et al., "Design of polydactyl zinc-finger proteins for unique addressing within complex genomes," Proc Natl Acad Sci USA, 94(11):5525-5530, 1997.
Livak and Schmittgen, "Analysis of relative gene expression data using real-time quantitative PCR and the 2(-Delta Delta C(T)) Method," *Method. Methods*, 25:402-408, 2001.
Mahfouz et al., "De novo-engineered transcription activator-like effector (TALE) hybrid nuclease with novel DNA binding specificity creates double-strand breaks," Proc Natl Acad Sci USA, 108:2623-2628, 2011.
Mahfouz et al., "TALE nucleases and next generation GM crops," *GM Crops*, 2(2):99-103, 2011.
Mak, "Sequence-specific DNA-binding TALEs," Nat Biotechnol, 29:43, 2011.
Marois et al., "The xanthomonas type III effector protein AvrBs3 modulates plant gene expression and induces cell hypertrophy in the susceptible host," Mol Plant Microbe Interact, 15(7):637-646, 2002.
Miller et al., "A TALE nuclease architecture for efficient genome editing," Nat Biotechnol, 29:143-148, 2011.
Miller et al., "An improved zinc-finger nuclease architecture for highly specific genome editing," Nature Biotechnol, 25:778-785, 2007.
Minczuk et al., "Development of a single-chain, quasi-dimeric zinc-finger nuclease for the selective degradation of mutated human mitochondrial DNA," Nucleic Acids Res, 36(12):3926-3938, 2008.
Mino et al., "Efficient double-stranded DNA cleavage by artificial zinc-finger nucleases composed of one zinc-finger protein and a single-chain FokI dimer," J Biotechnol, 140(3-4):156-161, 2009.
Moore et al., "Transactivated and chemically inducible gene expression in plants," Plant J, 45:651-683, 2006.
Morbitzer et al., "Assembly of custom TALE-type DNA binding domains by modular cloning," Nucleic Acids Research, 39(13):5790-5799, 2011.
Morbitzer et al., "Regulation of selected genome loci using de novo-engineered transcription activator-like effector (TALE)-type transcription factors," Proc Natl Acad Sci U S A., 107(50):21617-21622, 2010.
Moscou and Bogdanove, "A Simple Cipher Governs DNA Recognition by TAL Effectors," Science 326(5959): 1501, 2009.
Murakami et al., "The repeat domain of the type III effector protein PthA shows a TPR-like structure and undergoes conformational changes upon DNA interaction," Proteins, 78:3386-3395, 2010.
Murray et al., "Rapid isolation of high molecular weight plant DNA," *Nucl. Acids Res*, 8(19):4321-4325, 1980.
Mussolino et al., "A novel TALE nuclease scaffold enables high genome editing activity in combination with low toxicity," *Nucleic Acids Res*, 39:9283-9293, 2011.
Nakagawa et al., "Development of series of gateway binary vectors, pGWBs, for realizing efficient construction of fusion genes for plant transformation," J Biosci Bioeng, 104:34-41, 2007.
Niño-Liu et al., "Xanthomonas oryzae pathovars: model pathogens of a model crop," Mol Plant Pathol, 7(5):303-324, 2006.
Nissan et al. "The type III effectors HsvG and HsvB of gall-forming Pantoea agglomerans determine host specificity and function as transcriptional activators." Molecular Microbiology, 61(5): 1118-1131, 2006.

Noë et al., "XopC and XopJ, two novel type III effector proteins from Xanthomonas campestris pv. vesicatoria," J Bacteriol, 185(24):7092-7102, 2003.
Ovchinnikov et al., "PspXI, a novel restriction endonuclease that recognizes the unusual DNA sequence 5-VCTCGAGB-3," Bull Biotech Physio-Chemical Biol, 2005, 1(1):18-24, retrieved from the Internet: http://science.sibenzyme.com/article8_article_3_1.phtml.
Padidam, "Chemically regulated gene expression in plants," Curr Opin Plant Biol, 6:169-177, 2003.
Paques and Duchateau, "Meganucleases and DNA Double-Strand Break-Induced recombination: Perspectives for Gene Therapy," Curr Gene Ther, 7:49-66, 2007.
Park et al., "Avirulence gene diversity of Xanthomonas axonopodis pv. Glycines isolated in Korea," J Microbiol Biotechnol, 18(9):1500-1509, 2008.
Pattanayak et al., "Revealing off-target cleavage specificities of zinc-finger nucleases by in vitro selection," Nat Methods, 8:765-770, 2011.
Paulus et al., "Silencing β1,2-xylosyltransferase in transgenic tomato fruits reveals xylose as constitutive component in IgE-binding epitopes," *Fronties in Plant Science*, 2(42), 12 pages, 2011.
Pavletich and Pabo, "Zinc finger-DNA recognition: crystal structure of a Zif268-DNA complex at 2.1 A," Science, 252:809-817, 1991.
Pearson, "The fate of fingers," Nature, 455:160-164, 2008.
Pennisi, "The Tale of the TALES," Science, 338(6113):1408-1411, 2012.
Pham et al., "Mutant alleles of FAD2-1A and FAD2-1B combine to produce soybeans with the high oleic acid seed oil trait," *BMC Plant Biol.*, 10:195, 2010.
Pingoud and Silva, "Precision genome surgery," Nature Biotechnol, 25(7):743-744, 2007.
Podhajska and Szybalski, "Conversion of the FokI endonuclease to a universal restriction enzyme: cleavage of phage M13mp7 DNA at predetermined sites," Gene, 40(2-3):175-182, 1985.
Pomerantz et al., "Structure-based design of transcription factors," Science, 267(5194):93-96, 1995.
Porteus and Baltimore, "Chimeric nucleases stimulate gene targeting in human cells," Science, 300:763, 2003.
Porteus and Carroll, "Gene targeting using zinc finger nucleases," Nature Biotechnol, 23:967-973, 2005.
Porteus, "Zinc fingers on target," Nature, 459: 337-338, 2009.
Potenza et al., "Targeting transgene expression in research, agricultural, and environmental applications: Promoters used in plant transformation," In vitro Cell Dev Biol, 40(1):1-22, 2004.
Puchta et al., "Homologous recombination in plant cells is enhanced by in vivo induction of double strand breaks into DNA by a site-specific endonuclease," Nucl Acids Res, 21(22):5034-5040, 1993.
Radecke et al., "Zinc-finger nuclease-induced gene repair with oligodeoxynucleotides: wanted and unwanted target locus modifications," Mol Ther, 18(4):743-753, 2010.
Reyon et al., "FLASH assembly of TALENs for high-throughput genome editing," *Nat Biotechnol*, 30:460-465, 2012.
Römer et al., "Plant pathogen recognition mediated by promoter activation of the pepper Bs3 resistance gene," Science, 318(5850):645-648, 2007.
Römer et al., "A single plant resistance gene promoter engineered to recognize multiple TAL effectors from disparate pathogens," Proc Natl Acad Sci USA, 106(48):20526-31, 2009.
Römer et al., "Promoter elements of rice susceptibility genes are bound and activated by specific TAL effectors from the bacterial blight pathogen, Xanthomonas oryzae pv. oryzae," New Phytol, 187:1048-1057, 2010.
Römer et al., "Recognition of AvrBs3-Like Proteins Is Mediated by Specific Binding to Promoters of Matching Pepper Bs3 Alleles," Plant Physiol, 150:1697-1712, 2009.
Romero et al., "Temperature Sensitivity of the Hypersensitive Response of Bell Pepper to Xanthomonas axonopodis pv. vesicatoria," Phytopathology, 92(2):197-203, 2002.
Rossier et al., "HrpB2 and HrpF from Xanthomonas are type III-secreted proteins and essential for pathogenicity and recognition by the host plant," Mol Microbiol, 38(4):828-838, 2000.

(56) References Cited

OTHER PUBLICATIONS

Rossier et al., "The Xanthomonas Hrp type III system secretes proteins from plant and mammalian bacterial pathogens," Proc Natl Acad Sci USA, 96(16):9368-9373, 1999.
Rouet et al., "Expression of a site-specific endonuclease stimulates homologous recombination in mammalian cells," Proc Natl Acad Sci USA, 91(13):6064-6068, 1994.
Rouet et al., "Introduction of double-strand breaks into the genome of mouse cells by expression of a rare-cutting endonuclease," Mol Cell Biol, 14(12):8096-8106, 1994.
Rybak et al., "Identification of *Xanthomonas citri* ssp. citri host specificity genes in a heterologous expression host," Mol Plant Pathol, 10(2):249-262, 2009.
Sandhu et al., "Enhanced oleic acid content in the soybean mutant M23 is associated with the deletion in the Fad2-la gene encoding a fatty acid desaturase," *JAOCS*, 84:229-235, 2007.
Santiago et al., "Targeted gene knockout in mammalian cells by using engineered zinc-finger nucleases," Proc Natl Acad Sci USA, 105(15):5809-5814, 2008.
Scholze and Boch, "TAL effectors are remote controls for gene activation," Curr Opin Microbiol, 14:47-53, 2011.
Scholze and Boch. "TAL effector-DNA specificity," Virulence, 1(5):428-432, 2010.
Schornack et al., "Characterization of AvrHah1, a novel AvrBs3-like effector from Xanthomonas gardneri with virulence and avirulence activity," New Phytol, 179:546-556, 2008.
Schornack et al., "Expression levels of avrBs3-like genes affect recognition specificity in tomato Bs4- but not in pepper BS3-mediated perception," Mol Plant-Microbe Interact, 18(11):1215-1225, 2005.
Schornack et al., "Gene-for-gene-mediated recognition of nuclear-targeted AvrBs3-like bacterial effector proteins," *J. Plant Physiol*, 163:256-272, 2006.
Schornack et al., "The tomato resistance protein Bs4 is a predicted non-nuclear TIR-NB-LRR protein that mediates defense responses to severely truncated derivatives of AvrBs4 and overexpressed AvrBs3," Plant J, 37(1):46-60, 2004.
Segal et al., "Endonuclease-induced, targeted homologous extrachromosomal recombination in Xenopus oocytes," Proc Natl Acad Sci USA, 92(3):806-810, 1995.
Sera, "Inhibition of virus DNA replication by artificial zinc finger proteins," J Virol, 79(4):2614-2619, 2005.
Shepard and Totten, "Mesophyll cell protoplasts of potato: isolation, proliferation, and plant regeneration," *Plant Physiol.*, 60:313-316, 1977.
Shukla et al., "Precise genome modification in the crop species *Zea mays* using zinc-finger nucleases," Nature, 459(7245):437-441, 2009.
Simon et al., "Targeting DNA with triplex-forming oligonucleotides to modify gene sequence," Biochimie, 90:1109-1116, 2008.
Skipper, "Technology: The holy grail for plant biologists," Nature Reviews Genetics, 10(6):350, 2009.
Strasser et al., "Generation of glycol-engineered *Nicotiana bethamiana* for the production of monoclonal antibodies with a homogeneous human-like N-glycan structure," *Plant Biotechnology Journal*, 6:392-402, 2008.
Studholme et al., "Genome-wide sequencing data reveals virulence factors implicated in banana Xanthomonas wilt," FEMS Microbiol Lett., 310(2):182-192, 2010.
Sugio et al., "Two type III effector genes of Xanthomonas oryzae pv. oryzae control the induction of the host genes OsTFIIAgammal and OsTFX1 during bacterial blight of rice," *Proc Natl Acad Sci USA*, 104:10720-10725, 2007.
Swarup et al., "An Xanthomonas citri pathogenicity gene, pthA, pleiotropically encodes gratuitous avirulence on nonhosts," Mol Plant Microbe Interact, 5(3):204-213, 1992.
Szurek et al. "Type III-dependent translocation of the Xanthomonas AvrBs3 protein into the plant cell," Mol Microbiol, 46(1): 13-23, 2002.
Szurek et al., "Eukaryotic features of the Xanthomonas type III effector AvrBs3: protein domains involved in transcriptional activation and the interaction with nuclear import receptors from pepper," Plant J, 26(5):523-534, 2001.
Takenaka et al., "Inhibition of tomato yellow leaf curl virus replication by artificial zinc-finger proteins," Nucl Acids Symposium Series, 51(1):429-430, 2007.
Thieme et al., "New type III effectors from Xanthomonas campestris pv. vesicatoria trigger plant reactions dependent on a conserved N-myristoylation motif," Mol Plant Microbe Interact, 20(10):1250-1261, 2007.
Thierry et al., "Cleavage of yeast and bacteriophage T7 genomes at a single site using the rare cutter endonuclease I-Sce I," Nucl Acids Res, 19(1):189-190, 1991.
Tovkach et al., "A toolbox and procedural notes for characterizing novel zinc finger nucleases for genome editing in plant cells," Plant J, 57:747-757, 2009.
Townsend et al., "High-frequency modification of plant genes using engineered zinc-finger nucleases," Nature, 459:442-445, 2009.
Urnov et al., "Highly efficient endogenous human gene correction using designed zinc-finger nuclease," Nature, 435(7042):646-651, 2005.
Van Den Ackerveken et al., "Recognition of the bacterial avirulence protein AvrBs3 occurs inside the host plant cell," Cell, 87(7):1307-1316, 1996.
Van Den Elzen et al., "A chimaeric hygromycin resistance gene as a selectable marker in plant cells," *Plant Molecular Biology*, 5:299-302, 1985.
Vergunst et al., "VirB/D4-Dependent Protein Translocation from Agrobacterium into Plant Cells," Science, 290:979-982, 2000.
Voytas et al., "Plant science. DNA binding made easy," Science, 326(5959):1491-1492, 2009.
Wah et al., "Structure of FokI has implications for DNA cleavage," Proc Natl Acad Sci USA, 95(18):10564-10569, 1998.
Wah et al., "Structure of the multimodular endonuclease FokI bound to DNA," Nature, 388(3):97-100, 1997.
Wang et al., "Chemically regulated expression systems and their applications in transgenic plants," Transgenic Res, 12:529-540, 2003.
Weber et al., "The type III-dependent Hrp pilus is required for productive interaction of Xanthomonas campestris pv. vesicatoria with pepper host plants," J Bacteriol, 187(7):2458-2468, 2005.
White and Yang, "Host and pathogen factors controlling the rice/Xanthomonas oryzae interaction," Plant Physiol, 150:1677-1686, 2009.
White et al., "The type III effectors of Xanthomonas," Mol Plant Pathol, 10:749-766, 2009.
Wright et al., "High-frequency homologous recombination in plants mediated by zinc-finger nucleases," *Plant J*, 44:693-705, 2005.
Yang and White, "Diverse members of the AvrBs3/PthA family of type III effectors are major virulence determinants in bacterial blight disease of rice," Mol Plant Microbe Interact, 17(11):1192-1200, 2004.
Yang et al. "The virulence factor AvrXa7 of Xanthomonas oryzae of Oryzae is a type III secretion pathway-dependent nuclear-localized double stranded DNA binding protein," Proc Natl Acad Sci USA, 97(17): 9807-9812, 2000.
Yang et al., "Avoidance of host recognition by alterations in the repetitive and C-terminal regions of AvrXa7, a type III effector of Xanthomonas oryzae pv. oryzae," Mol Plant Microbe Interact, 18(2):142-149, 2005.
Yang et al., "Os8N3 is a host disease-susceptibility gene for bacterial blight of rice," *Proc Natl Acad Sci USA*, 103:10503-10508, 2006.
Yoo et al., "Arabidopsis mesophyll protoplasts: a versatile cell system for transient gene expression analysis," *Nature Protocols*, 2:1565-1572, 2007.
Yuan et al., "Characterization of Xanthomonas oryzae-responsive cis-acting element in the promoter of rice race-specific susceptibility gene Xa13," Mol Plant, 4(2):300-309, 2011.
Zhang et al., "Efficient construction of sequence-specific TAL effectors for modulating mammalian transcription.," *Nat Biotechnol*, 29:149-153, 2011.

(56) References Cited

OTHER PUBLICATIONS

Zhang et al., "High frequency targeted mutagenesis in *Arabidopsis thaliana* using zinc finger nucleases," *Proc Natl Acad Sci USA*, 107(26):12028-12033, 2010.
Zhang et al., "RNAi effects on regulation of endogenous acid invertase activity in potato (*Solanum tuberosum* L.) tubers," *Chin J Agric. Biotechnol*, 5:107-111, 2008.
Zhu et al., "The C terminus of AvrXa10 can be replaced by the transcriptional activation domain of VP16 from the herpes simplex virus," Plant Cell, 11(9):1665-1674, 1999.
Zhu et al., "AvrXa10 Contains an Acidic Transcriptional Activation Domain in the Functionally Conserved C Terminus," Molecular Plant-Microbe Interactions, 11(8): 824-832, 1998.
Zhu et al., "The rsma-like gene rsmA(XOO) of Xanthomonas oryzae pv. oryzae regulates bacterial virulence and production of diffusible signal factor," Mol Plant Pathol, 12(3):227-237, 2011, Epub 2010.
Zou et al., "Identification of an avirulence gene, avrxa5, from the rice pathogen Xanthomonas oryzae pv. oryzae," Sci China Life Sci, 53(12):1440-1449, 2010.
Zrenner et al., "Soluble acid intervase determines the hexos-to sucrose ratio in cold-stored potato tubers," *Planta*, 198(2):246-252, 1996.
Zuo and Chua, "Chemical-inducible systems for regulated expression of plant genes," Curr Opin Biotechnol, 11:146-151, 2000.
Zuo et al., "Technical advance: An estrogen receptor-based transactivator XVE mediates highly inducible gene expression in transgenic plants," *Plant J.* 24:265-273, 2000.
Bachlava et al, "Mapping genes encoding microsomal ω-6 desaturase enzymes and their cosegregation with QTL affecting oleate content in soybean," *Crop Science*, 48: 640-650, Mar.-Apr. 2008.
Bolon et al., "Phenotypic and genomic analyses of a fast neutron mutant population resource in soybean1[W][OA]," *Plant Physiology*, 156: 240-253, May 2011.
Goettel et el., "Identification and characterization of large DNA deletions affecting oil quality traits in soybean seeds through transcriptome sequencing analysis," *Theor Appl Genet*, 129: 1577-1593, 2016.
Haun et al., "Improved soybean oil quality by targeted mutagenesis of the fatty acid desaturase 2 gene family," *Plant Biotechnology Journal*, 12:934-940, 2014.
Hoshino et al., "Novel GmFAD2-1b mutant alleles created by reverse genetics induce marked elevation of oleic acid content in soybean seeds in combination with GmFAD2-1a mutant alleles," *Breeding Science*, 60: 419-425, 2010.
Kebede et al., "A new gene that controls seed coat wrinkling in soybean," *Euphytica*, 189:309-320, 2013.
Scherder et al., "Agronomic and seed characteristics of soybean lines with increased oleate content," *Crop Science*, 48: 1755-1758, Sep.-Oct. 2008.

\* cited by examiner

Figure 1A

FAD2_1A_T1
TTCATTTCTACATTGCCACCACTACTTCCACCTCCTTCCTCAACCCTTTTCcctcaTTGCATGGCCAATCTATTGGGTTC
TCCAAGGTTGCCTTCTCACTGGTGTGGGTGATTGCTCACGAGTGGTCACCATGCCTTCAGCAAGTACCAATGGG
TTGATGATGTTGTGGGTTTGACCCTTCACTCAACACTTTAGTCCCTATTTCTCATGGAAAATAAGCCATCGcggcCATC
ACTCCAACACAGGTTCCCTTGACCGTGATGAAGTGTTTGTCCCAAAAC FAD2_1A_T2
TTCATTTTCTACATTGCCACCACTACTTCCACCTCCTTCCTCAACCCTTTTCcctcaTTGCATGGCCAATCTATTGGGTTC
TCCAAGGTTGCCTTCTCACTGGTGTGGGTGATTGCTCACGAGTGGTCACCATGCCTTCAGCAAGTACCAATGGG
TTGATGATGTTGTGGGTTTGACCCTTCACTCAACACTTTAGTCCCTATTTCTCATGGAAAATAAGCCATCGcggcCATC
ACTCCAACACAGGTTCCCTTGACCGTGATGAAGTGTTTGTCCCAAAAC FAD2_1A_T3
TTCATTTTCTACATTGCCACCACTACTTCCACCTCCTTCCTCAACCCTTTTCcctcaTTGCATGGCCAATCTATTGGGTTC
TCCAAGGTTGCCTTCTCACTGGTGTGGGTGATTGCTCACGAGTGGTCACCATGCCTTCAGCAAGTACCAATGGG
TTGATGATGTTGTGGGTTTGACCCTTCACTCAACACTTTAGTCCCTATTTCTCATGAAAATAAGCCATCGcggcCATC
ACTCCAACACAGGTTCCCTTGACCGTGATGAAGTGTTTGTCCCAAAAC FAD2_1A_T4
TTCATTTTCTACATTGCCACCACTACTTCCACCTCCTTCCTCAACCCTTTTCcctcaTTGCATGGCCAATCTATTGGGTTC
TCCAAGGTTGCCTTCTCACTGGTGTGGGTGATTGCTCACGAGTGGTCACCATGCCTTCAGCAAGTACCAATGGG
TTGATGATGTTGTGGGTTTGACCCTTCACTCAACACTTTAGTCCCTATTTCTCATGAAAATAAGCCATCGcggcCATC
ACTCCAACACAGGTTCCCTTGACCGTGATGAAGTGTTTGTCCCAAAAC

Figure 1B

FAD2_1B_T1
TTCATTTTCTACATTGCCACCACCTACTTCCACCTCCTCCCtaccCCTTTTCCCTCATTGCATGGCCAATCTATTGGGTTCT
CCAAGGTTGCATTCTTACTGGCGTGTGGGTGATTGCTCACGAGTGTGGTCACCATGCCTTCAGCAAGTACCCATGGGTT
GATGATGTTATGGGTTTGACCGTTCACTCAGCACTTTAGTCCCTTATTTCTCATGGAAAATAAGCCATCGccgcCACCACT
CCAACACGGGTTCCCTTGACCGTGATGAAGTGTTTGTCCCAAAAC FAD2_1B_T2
TTCATTTTCTACATTGCCACCACCTACTTCCACCTCCTCCCtaccCCTTTTCCCTCATTGCATGGCCAATCTATTGGGTTCT
CCAAGGTTGCATTCTTACTGGCGTGTGGGTGATTGCTCACGAGTGTGGTCACCATGCCTTCAGCAAGTACCCATGGGTT
GATGATGTTATGGGTTTGACCGTTCACTCAGCACTTTAGTCCCTTATTTCTCATGGAAAATAAGCCATCGccgcCACCACT
CCAACACGGGTTCCCTTGACCGTGATGAAGTGTTTGTCCCAAAAC FAD2_1B_T3
TTCATTTTCTACATTGCCACCACCTACTTCCACCTCCTCCCtaccCCTTTTCCCTCATTGCATGGCCAATCTATTGGGTTCT
CCAAGGTTGCATTCTTACTGGCGTGTGGGTGATTGCTCACGAGTGTGGTCACCATGCCTTCAGCAAGTACCCATGGGTT
GATGATGTTATGGGTTTGACCGTTCACTCAGCACTTTAGTCCCTTATTTCTCATGGAAAATAAGCCATCGccgcCACCACT
CCAACACGGGTTCCCTTGACCGTGATGAAGTGTTTGTCCCAAAAC FAD2_1B_T4
TTCATTTTCTACATTGCCACCACCTACTTCCACCTCCTCCCtaccCCTTTTCCCTCATTGCATGGCCAATCTATTGGGTTCT
CCAAGGTTGCATTCTTACTGGCGTGTGGGTGATTGCTCACGAGTGTGGTCACCATGCCTTCAGCAAGTACCCATGGGTT
GATGATGTTATGGGTTTGACCGTTCACTCAGCACTTTAGTCCCTTATTTCTCATGGAAAATAAGCCATCGccgcCACCACT
CCAACACGGGTTCCCTTGACCGTGATGAAGTGTTTGTCCCAAAAC

Figure 2

|  | Treatment | |
|---|---|---|
|  | FAD2_T01<br>a b c WT | FAD2_T04<br>a b c d e f WT |
| Target — FAD2-1A | A | B |
| FAD2-1B | C | D |

Figure 3

```
FAD2-1A (FAD2_T1_C40)                                                                                      Deletions/
                                                                                                           Inserts    SEQ ID NO:
GCCACCACCTACTTCCACCTCCTTCCCTCAACCCTTTTCCCTCATTGCATGGCCAATCTATTGGGTTCTCCAAGGTT                              0          3
GCCACCACCTACTTCCACCTCCTTCCTCAA------GATT------------GCCAATCTATTGGGTTCTCCAAGGTT                             -16/+4     4
GC-----------------------------------------------------ATGGCCAATCTATTGGGTTCTCCAAGGTT                       -45        5

FAD2-1B (FAD2_T1_C40)
GCCACCACCTACTTCCACCTCCTCCCTCACCCCTTTTCCCTCATTGCATGGCCAATCTATTGGGTTCTCCAAGGTT                               0          3
GCCACCACCTACTTCCACCTCCTCCCTCA--------------TTGCATGGCCAATCTATTGGGTTCTCCAAGGTT                               -14        6

FAD2-1A (FAD2_T4_C11)
ATTTCTCATGGAAAATAAGCCATCGCCGCCATCACTCCAACACAGGTTCCCTTGACCGTGATGAAGTGTTTGTCCC                               0          7
ATTTCTCATGGAAAATAAGCCATCGCCGCCATCGCCGCCATCACTCACTCCAACAC--------TTGACCGTGATGAAGTGTTTGTCCC                  -8         8
ATTTCTCATGGAAAATAAGCCATCGCCGCCATCGCCGC-------------------------------GATGAAGTGTTTGTCCC                    -30        9

FAD2-1B (FAD2_T4_C11)
ATTTCTCATGGAAAATAAGCCATCGCCGCCATCACTCCAACACAGGTTCCCTTGACCGTGATGAAGTGTTTGTCCC                               0          7
ATTTCTCATGGAAAATAAGCCATCGCCGCCATCGCCGCCACCACTCCAACAC------CCTTGACCGTGATGAAGTGTTTGTCCC                      -6         10
ATTTCTCATGGAAAATAAGCCATCGCCGCCATC-------------------------------------TGAAGTGTTTGTCCC                     -92        11
ATTTCTCATGGAAAATAA--------------------------------CACGGGTTCCCTTGACCGTGATGAAGTGTTTGTCCC                     -22        12
```

Figure 5

```
GM026-18                                                                                                          SEQ ID NO:
Sequence (FAD2-1A)
ATTTCTCATGGAAAATAAGCCATCGCCGCGCCATCACTCCAACACAGGTTCCCTTGACCGTGATGAAGTGTTTGTCCCA                                        13
--------------------------------------------------------------------------CTTGACCGTGATGAAGTGTTTGTCCCA                  14

Sequence (FAD2-1B)
ATTTCTCATGGAAAATAAGCCATCGCCGCCACCACTCCAACACGGGTTCCCTTGACCGTGATGAAGTGTTTGTCCCA                                          15
ATTTCTCATGGAAAATAAGCCATCGCC-----------------------------------------CTTGACCGTGATGAAGTGTTTGTCCCA                        16

GM026-23
Sequence (FAD2-1A)
ATTTCTCATGGAAAATAAGCCATCGCCGCGCCATCACTCCAACACAGGTTCCCTTGACCGTGATGAAGTGTTTGTCCCA                                        13
ATTTCTCATGGAAAATAAGCCATCGCC----T--------CAGGTTCCCTTGACCGTGATGAAGTGTTTGTCCCA                                            17

GM027-06
Sequence (FAD2-1B)
ATTTCTCATGGAAAATAAGCCATCGCCGCCACCACTCCAACACGGGTTCCCTTGACCGTGATGAAGTGTTTGTCCCA                                          15
ATTTCTCATGGAAAATAAGCCATCGCC-----------------------------------------CTTGACCGTGATGAAGTGTTTGTCCCA                        16
```

MODIFYING SOYBEAN OIL COMPOSITION THROUGH TARGETED KNOCKOUT OF THE FAD2-1A/1B GENES

CROSS-REFERENCE TO RELATED APPLICATIONS

This application claims benefit of priority from U.S. Provisional Application Ser. No. 61/790,655, filed on Mar. 15, 2013.

TECHNICAL FIELD

This document relates to materials and methods for making soybean plants that can be used to produce oil having a modified composition as compared to wild type plants. This document also relates to soybean varieties that lack FAD2-1A/1B activity.

BACKGROUND

Soybean (*Glycine max*) is an important legume crop worldwide due to its ability to fix atmospheric nitrogen. Soybeans also serve as a major source of animal feed protein, and its oil has uses ranging from cooking/frying to industrial uses and biodiesel. Typically, a hydrogenation process is used to increase heat stability and improve shelf life and taste of soybean oil. However, hydrogenation increases the cost of production and also results in the formation of trans fats, which have been linked to cardiovascular disease in humans.

SUMMARY

Provided herein are materials and methods for modifying soybean oil composition by reducing or eliminating expression of the delta-twelve fatty acid desaturase 2 (FAD2) 1A and 1B genes without the use of transgenesis. Soybean varieties having such modified oil composition also are provided.

The methods described herein utilize sequence-specific, rare-cutting endonucleases to introduce mutations in the FAD2-1A and/or FAD2-1B coding sequences, thereby knocking out gene function. These methods mediate FAD2-1A/1B silencing without insertion of a transgene, which would not be acceptable in Europe and other regions of the world. The methods described herein also can be more cost-effective than transgenic approaches.

In one aspect, this document features a soybean plant, plant part, or plant cell having a mutation in one or more FAD2-1A alleles, a mutation in one or more FAD2-1B alleles, or a mutation in one or more FAD2-1A alleles and a mutation in one or more FAD2-1B alleles, wherein the plant, plant part, or plant cell produces oil that has increased oleic acid content and decreased linoleic acid content as compared to oil produced from a corresponding wild type soybean plant, plant part, or plant cell. Each mutation can be at a sequence in SEQ ID NO:1 or SEQ ID NO:2. Each mutation can be induced by a rare-cutting endonuclease (e.g., a transcription activator-like (TAL) effector endonuclease). The TAL effector endonuclease can bind to a sequence as set forth in any of SEQ ID NOS:18-33. Each mutation can be a deletion of more than one nucleotide. Each FAD2-1A and FAD2-1B allele can have a deletion of an endogenous nucleic acid sequence, without including any exogenous nucleic acid. The plant part can be a seed.

In another aspect, this document features a soybean plant, plant part, or plant cell having a mutation in one or more FAD2-1A alleles, a mutation in one or more FAD2-1B alleles, or a mutation in one or more FAD2-1A alleles and a mutation in one or more FAD2-1B alleles, wherein the plant, plant part, or plant cell produces oil that has an oleic acid content of greater than 30% (e.g., greater than 40%, greater than 50%, or greater than 55%).

In another aspect, this document features a soybean plant, plant part, or plant cell having a mutation in one or more FAD2-1A alleles, a mutation in one or more FAD2-1B alleles, or a mutation in one or more FAD2-1A alleles and a mutation in one or more FAD2-1B alleles, wherein the plant, plant part, or plant cell produces oil that has a linoleic acid content of less than 10% (e.g., less than 5%, less than 3%, or less than 1%).

In another aspect, this document features a method for producing soybean oil having increased oleic acid content and reduced linoleic acid content. The method can include (a) providing a soybean plant or plant part having a mutation in one or more FAD2-1A alleles, a mutation in one or more FAD2-1B alleles, or a mutation in one or more FAD2-1A alleles and a mutation in one or more FAD2-1B alleles; and (b) producing oil from the plant or plant part. Each mutation can be induced by a rare-cutting endonuclease (e.g., a TAL effector endonuclease). The TAL effector endonuclease can bind to a sequence as set forth in any of SEQ ID NOS:18-33.

In still another aspect, this document features a method for making a soybean plant having a mutation in each FAD2-1A allele and a mutation in each FAD2-1B allele. The method can include (a) contacting a population of soybean plant cells having functional FAD2-1A and FAD2-1B alleles with one or more rare-cutting endonucleases targeted to endogenous FAD2-1A sequences, and one or more rare-cutting endonucleases targeted to endogenous FAD2-1B sequences, (b) selecting, from the population, a cell in which each FAD2-1A allele and each FAD2-1B allele has been inactivated, and (c) regenerating the selected plant cell into a soybean plant. The soybean plant cells can contain cotyledon cells. The method can include transforming cotyledon cells with one or more vectors encoding the one or more rare-cutting endonucleases. The one or more rare-cutting endonucleases can be TAL effector endonucleases. Each of the TAL effector endonucleases can be targeted to a sequence as set forth in any of SEQ ID NOS:18-33. The method can include introducing into the plant cells one or more TAL effector endonuclease proteins. The method can further include culturing the plant cells to generate plant lines. The method can further include isolating genomic DNA containing at least a portion of the FAD2-1A locus or at least a portion of the FAD2-1B locus from the plant cells.

This document also features a method for generating a soybean plant having a mutation in each FAD2-1A allele and a mutation in each FAD2-1B allele. The method can include (a) crossing a first soybean plant having a mutation in at least one FAD2-1A allele and a mutation in at least one FAD2-1B allele with a second soybean plant having a mutation in at least one FAD2-1A allele and a mutation in at least one FAD2-1B allele, to obtain progeny; and (b) selecting from the progeny a soybean plant that has a mutation in each FAD2-1A and FAD2-1B allele. Each mutation can be induced by a rare-cutting endonuclease (e.g., a TAL effector endonuclease). The TAL effector endonuclease can bind to a sequence as set forth in any of SEQ ID NOS:18-33. Each mutation can be a deletion of more than one nucleotide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows DNA sequences for various TAL effector endonuclease target sites in FAD2-1A and FAD2-1B. DNA sequence from the FAD2-1A gene (SEQ ID NO:1) is shown in FIG. 1A, and DNA sequence from the FAD2-1B gene (SEQ ID NO:2) is shown in FIG. 1B. The underlined sequences indicate target sites for TAL effector endonucleases. Lower case letters denote restriction endonuclease sites used to screen for TAL effector endonuclease-induced mutations.

FIG. 2 is a picture of a gel showing products from a PCR enrichment assay used to screen soybean hairy roots for TAL effector endonuclease-induced mutations in FAD2-1A and FAD2-1B.

FIG. 3 shows exemplary DNA sequences of TAL effector endonuclease-induced mutations in the FAD2-1A and FAD2-1B genes in soybean hairy roots. The top line of each panel shows the DNA sequence of the recognition site for the TAL effector endonucleases (underlined) in FAD2-1A (top two panels) and FAD2-1B (bottom two panels). The other sequences show representative mutations that were induced by imprecise non-homologous end joining (NHEJ), with the sizes of deletions given on the right.

FIG. 5 shows DNA sequences of TAL effector endonuclease-induced mutations in FAD2-1A and FAD2-1B. These mutations were genetically transmissible.

DETAILED DESCRIPTION

Figure 4:
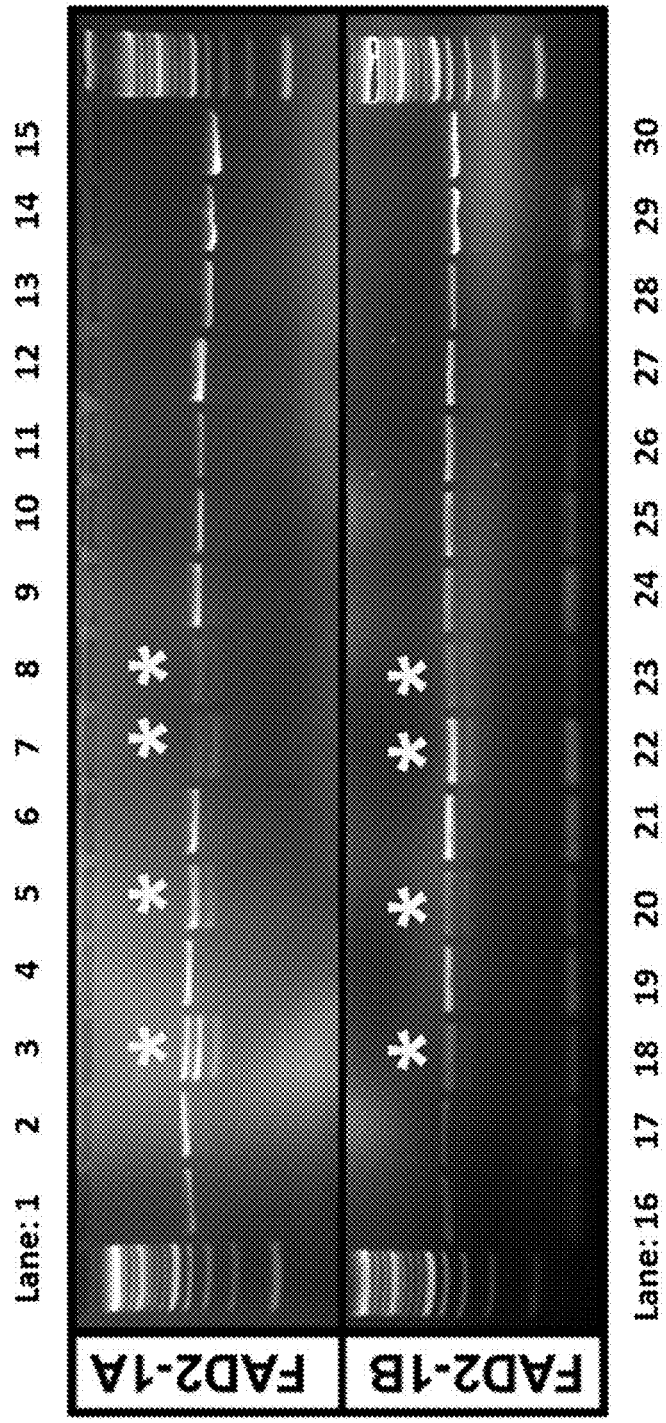
FIG. 4 is a picture of a gel showing the result of a T7E1 assay performed on regenerated soybean plants to identify TAL effector endonuclease-induced mutations in FAD2-1A and FAD2-1B. Table 4A herein provides information about which regenerated plant and which particular FAD2-1 gene were analyzed in each lane of the gel. The first and last lanes are molecular length markers and are not numbered. DNA samples listed as "uncut" in Table 4A were not treated with T7E1.

Commodity soybean oil is made up of five fatty acids: palmitic acid (10%), stearic acid (4%), oleic acid (18%), linoleic acid (55%) and linolenic acid (13%). Plant oils with high oleic acid content may require less processing to improve stability and/or taste. Such oils also may be healthier, as well as better suited for the production of biodiesel. Soybean oil having an oleic acid content of greater than 55% and a linoleic acid content of less than 10% can be particularly useful. Traditional breeding and mutagenesis strategies have been used to generate soybean varieties containing elevated levels of oleic acid, but these varieties have reduced yield and thus have not been acceptable to farmers.

The enzymes responsible for the biosynthetic progression from palmitic acid to linolenic acid have been identified. For example, the FAD2 genes are responsible for converting oleic acid precursors to linoleic acid precursors during oil accumulation in developing soybean seeds. Due to the ancient polyploidization of soybean, two copies of FAD2 (FAD2-1A and FAD2-1B) exist in the soybean genome. These genes have about 95% sequence identity at the DNA level, and the encoded proteins have about 99% sequence identity at the amino acid level. Plants homozygous for naturally occurring FAD2-1B mutant alleles can have a modest increase (20.5% to 29.4%) in oleic acid composition, as described elsewhere (Pham et al., *BMC Plant Biol.* 10:195, 2010). Mutations in FAD2-1A have been developed through X-ray mutagenesis and TILLing, to produce seeds containing up to 50% oleic acid (Sandhu et al., *JAOCS* 84:229-235, 2007), and mutating both the FAD2-1A and FAD2-1B alleles resulted in oil with an oleic acid content of 82.2% (Pham et al., supra).

This document provides soybean plants that have reduced (e.g., lack) FAD2-1A and/or FAD2-1B activity, as well methods for generating such plants, and oil derived from such plants. The methods described herein can be used to generate soybean varieties having oil with an increased oleic acid component of at least 30% (e.g., at least 35%, at least 40%, at least 45%, at least 50%, or at least 55%, and a reduction in linoleic acid component to 10% or less (e.g., 8% or less, 5% or less, 4% or less, 3% or less, 2% or less, 1% or less, or 0.5% or less). In some embodiments, this modification of soybean oil composition can be achieved by completely knocking out the expression of the FAD2-1A and/or FAD2-1B genes. According to some of the methods provided herein, both alleles of FAD2-1A and/or FAD2-1B genes are inactivated using non-transgenic techniques. Removing the all RNA transcripts of FAD2-1A/1B can severely reduce the conversion of oleic acid precursors to linoleic acid precursors in soybean seeds.

To accomplish the complete elimination of FAD2-1A/1B expression, for example, an engineered, rare-cutting nuclease was designed to recognize a conserved region of both FAD2-1 genes and create a double-strand break. Improper repair due to Non-Homologous End Joining (NHEJ) at the DNA break site generates missense and/or nonsense mutations in the FAD2-1A/1B coding regions, rendering the FAD2-1A/1B RNA transcripts unstable and targeted for degradation prior to translation.

In soybean, there are at least two members (1A and 1B) in the FAD2 gene family. Representative examples of naturally occurring soybean FAD2-1A and FAD2-1B nucleotide sequences are shown in Table 5. The soybean plants, cells, plant parts, seeds, and progeny thereof provided herein can have a mutation in each of the endogenous FAD2-1A and FAD2-1B alleles, such that expression of each gene is reduced or completely inhibited. Alternatively, the soybean plants, cells, plant parts, seeds, and progeny thereof provided herein may have a mutation in at least one FAD2-1A allele and/or in at least one FAD2-1B allele, such that expression of each gene is reduced or completely inhibited. The soybean plants, cells, parts, seeds, and progeny can have increased levels of oleic acid and reduced levels of linoleic acid as compared to wild type soybean plants, cells, parts, seeds, and progeny.

The plants, plant cells, plant parts, seeds, and plant progeny provided herein can be generated using a TAL effector endonuclease system to make targeted knockouts in the FAD2-1A and/or FAD2-1B genes. Thus, this disclosure provides materials and methods for using TAL effector endonucleases to generate plants and related products (e.g., seeds and plant parts) that are particularly suitable for production of soybean oil with increased oleic acid content and decreased linoleic acid content. Other rare cutting, sequence-specific nucleases can be used to generate the desired plant material, including engineered homing endonucleases or zinc finger nucleases.

"Plants" and "plant parts" refers to cells, tissues, organs, seeds, and severed parts (e.g., roots, leaves, and flowers) that retain the distinguishing characteristics of the parent plant. "Seed" refers to any plant structure that is formed by continued differentiation of the ovule of the plant, following its normal maturation point at flower opening, irrespective of whether it is formed in the presence or absence of fertilization and irrespective of whether or not the seed structure is fertile or infertile.

The term "allele(s)" means any of one or more alternative forms of a gene at a particular locus. In a diploid (or amphidiploid) cell of an organism, alleles of a given gene are located at a specific location or locus on a chromosome. One allele is present on each chromosome of the pair of homologous chromosomes. "Heterozygous" alleles are two different alleles residing at a specific locus, positioned individually on corresponding pairs of homologous chromosomes. "Homozygous" alleles are two identical alleles residing at a specific locus, positioned individually on corresponding pairs of homologous chromosomes in the cell.

"Wild type" as used herein refers to a typical form of a plant or a gene as it most commonly occurs in nature. A "wild type FAD2-1A allele" is a naturally occurring FAD2-1A allele (e.g., as found within naturally occurring soybean plants) that encodes a functional FAD2-1A protein, while a "mutant FAD2-1A allele" is a FAD2-1A allele that does not encode a functional FAD2-1A protein. Such a "mutant FAD2-1A allele" can include one or more mutations in its nucleic acid sequence, where the mutation(s) result in no detectable amount of functional FAD2-1A protein in the plant or plant cell in vivo.

The term "rare-cutting endonucleases" herein refer to natural or engineered proteins having endonuclease activity directed to nucleic acid sequences having a recognition sequence (target sequence) about 12-40 bp in length (e.g., 14-40 bp in length). Typical rare-cutting endonucleases cause cleavage inside their recognition site, leaving 4 nt staggered cut with 3'OH or 5'OH overhangs. These rare-cutting endonucleases may be meganucleases, such as wild type or variant proteins of homing endonucleases, more particularly belonging to the dodecapeptide family (LAGLIDADG (SEQ ID NO:37); see, WO 2004/067736) or may result from fusion proteins that associate a DNA binding domain and a catalytic domain with cleavage activity. TAL-effector endonucleases and zinc-finger-nucleases (ZFN) are examples of fusions of DNA binding domains with the catalytic domain of the endonuclease FokI. Customized TAL effector endonucleases are commercially available under the trade name TALEN™ (Cellectis, Paris, France). For a review of rare-cutting endonucleases, see Baker, *Nature Methods* 9:23-26, 2012.

"Mutagenesis" as used herein refers to processes in which mutations are introduced into a selected DNA sequence. Mutations induced by endonucleases generally are obtained by a double strand break, which results in in-deletions ("indels") that can be detected by deep-sequencing analysis. Such mutations typically are deletions of several base pairs, and have the effect of inactivating the mutated allele. In the methods described herein, for example, mutagenesis occurs via double stranded DNA breaks made by TAL effector endonucleases targeted to selected DNA sequences in a plant cell. Such mutagenesis results in "TAL effector endonuclease-induced mutations" (e.g., TAL effector endonuclease-induced knockouts) and reduced expression of the targeted gene. Following mutagenesis, plants can be regenerated from the treated cells using known techniques (e.g., planting seeds in accordance with conventional growing procedures, followed by self-pollination).

In some cases, a nucleic acid can have a nucleotide sequence with at least about 75 percent sequence identity to a representative FAD2-1A or FAD2-1B nucleotide sequence. For example, a nucleotide sequence can have at least 75, at least 80, at least 85, at least 90, at least 91, at least 92, at least 93, at least 94, at least 95, at least 96, at least 97, at least 98, or at least 99 percent sequence identity to a representative, naturally occurring FAD2-1A or FAD2-1B nucleotide sequence as set forth in Table 3.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 250 matches when aligned with the sequence set forth in SEQ ID NO:1 is 86.5 percent identical to the sequence set forth in SEQ ID NO:1 (i.e., 250÷289×100=86.5). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

Methods for selecting endogenous target sequences and generating TAL effector endonucleases targeted to such sequences can be performed as described elsewhere. See, for example, PCT Publication No. WO 2011/072246 (which is incorporated herein by reference in its entirety). TAL effectors are found in plant pathogenic bacteria in the genus *Xanthomonas*. These proteins play important roles in disease, or trigger defense, by binding host DNA and activating effector-specific host genes (see, e.g., Gu et al., *Nature* 435:1122-1125, 2005; Yang et al., *Proc. Natl. Acad. Sci. USA* 103:10503-10508, 2006; Kay et al. *Science* 318:648-651, 2007; Sugio et al., *Proc. Natl. Acad. Sci. USA* 104: 10720-10725, 2007; and Römer et al. *Science* 318:645-648, 2007). Specificity depends on an effector-variable number of imperfect, typically 34 amino acid repeats (Schornack et al., *J. Plant Physiol.* 163:256-272, 2006; and WO 2011/072246). Polymorphisms are present primarily at repeat positions 12 and 13, which are referred to herein as the repeat variable-diresidue (RVD).

The RVDs of TAL effectors correspond to the nucleotides in their target sites in a direct, linear fashion, one RVD to one nucleotide, with some degeneracy and no apparent context dependence. This mechanism for protein-DNA recognition enables target site prediction for new target specific TAL effectors, as well as target site selection and engineering of new TAL effectors with binding specificity for the selected sites.

TAL effector DNA binding domains can be fused to other sequences, such as endonuclease sequences, resulting in chimeric endonucleases targeted to specific, selected DNA sequences, and leading to subsequent cutting of the DNA at or near the targeted sequences. Such cuts (i.e., double-stranded breaks) in DNA can induce mutations into the wild type DNA sequence via NHEJ or homologous recombination, for example. In some cases, TAL effector endonucleases can be used to facilitate site directed mutagenesis in complex genomes, knocking out or otherwise altering gene function with great precision and high efficiency. As described in the Examples below, TAL effector endonucleases targeted to the soybean FAD2-1A and FAD2-1B alleles can be used to mutagenize the endogenous genes, resulting in plants with reduced expression (e.g., without detectable expression) of these genes. The fact that some endonucleases (e.g., FokI) function as dimers can be used to enhance the target specificity of the TAL effector endonuclease. For example, in some cases a pair of TAL effector endonuclease monomers targeted to different DNA sequences (e.g., the underlined target sequences shown in FIGS. 1A and 1B) can be used. When the two TAL effector endonuclease recognition sites are in close proximity, as depicted in FIGS. 1A and 1B, the inactive monomers can come together to create a functional enzyme that cleaves the DNA. By requiring DNA binding to activate the nuclease, a highly site-specific restriction enzyme can be created.

The term "expression" as used herein refers to the transcription of a particular nucleic acid sequence to produce sense or antisense mRNA, and/or the translation of a sense mRNA molecule to produce a polypeptide (e.g., a therapeutic protein), with or without subsequent post-translational events.

"Reducing the expression" of a gene or polypeptide in a plant or a plant cell includes inhibiting, interrupting, knocking-out, or knocking-down the gene or polypeptide, such that transcription of the gene and/or translation of the encoded polypeptide are reduced as compared to a corresponding wild type plant or plant cell. Expression levels can be assessed using methods such as, for example, reverse transcription-polymerase chain reaction (RT-PCR), Northern blotting, dot-blot hybridization, in situ hybridization, nuclear run-on and/or nuclear run-off, RNase protection, or immunological and enzymatic methods such as ELISA, radioimmunoassay, and western blotting.

Methods for using TAL effector endonucleases to generate plants, plant cells, or plant parts having mutations in endogenous genes include, for example, those described in the Examples herein. For example, nucleic acids encoding TAL effector endonucleases targeted to selected FAD2-1A or FAD2-1B sequences (e.g., the FAD2-1A sequences shown in FIG. 1A or the FAD2-1B sequences shown in FIG. 1B) can be transformed into plant cells (e.g., cells in cotyledons), where they can be expressed. The cells subsequently can be analyzed to determine whether mutations have been introduced at the target site(s), through nucleic acid-based assays or protein-based assays to detect expression levels as described above, for example, or using nucleic acid-based assays (e.g., PCR and DNA sequencing, or PCR followed by a T7E1 assay; Mussolino et al., *Nucleic Acids Res* 39:9283-9293, 2011) to detect mutations at the genomic loci.

The mutagenized population, or a subsequent generation of that population, can be screened for a desired trait(s) (e.g., plants that have altered oil composition) that results from the mutations. Alternatively, the mutagenized population, or a subsequent generation of that population, can be screened for a mutation in a FAD2-1A or FAD2-1B gene. For example, the progeny $M_2$ generation of $M_1$ plants may be evaluated for the presence of a mutation in a FAD2-1A or FAD2-1B gene. A "population" is any group of individuals that share a common gene pool. As used herein, "$M_0$" refers to plant cells (and plants grown therefrom) exposed to a TAL effector nuclease, while "$M_1$" refers to seeds produced by self-pollinated $M_0$ plants, and plants grown from such seeds. "$M_2$" is the progeny (seeds and plants) of self-pollinated $M_1$ plants, "$M_3$" is the progeny of self-pollinated $M_2$ plants, and "$M_4$" is the progeny of self-pollinated $M_3$ plants. "$M_5$" is the progeny of self-pollinated $M_4$ plants. "$M_6$", "$M_7$", etc. are each the progeny of self-pollinated plants of the previous generation. The term "selfed" as used herein means self-pollinated.

One or more $M_1$ soybean plants can be obtained from individual, mutagenized $M_0$ plant cells (and plants grown therefrom), and at least one of the plants can be identified as containing a mutation in a FAD2-1A or FAD2-1B gene. An $M_1$ soybean plant may be heterozygous for a mutant allele at a FAD2-1A and/or a FAD2-1B locus and, due to the presence of the wild-type allele, exhibit delta-twelve fatty acid desaturase activity. Alternatively, an $M_1$ soybean plant may have a mutant allele at a FAD2-1A or FAD2-1B locus and exhibit the phenotype of lacking delta-twelve fatty acid desaturase activity. Such plants may be heterozygous and lack delta-twelve fatty acid desaturase activity due to phenomena such a dominant negative suppression, despite the presence of the wild-type allele, or may be homozygous due to independently induced mutations in both alleles at the FAD2-1A or FAD2-1B locus.

A soybean plant carrying mutant FAD2-1A and FAD2-1B alleles can be used in a plant breeding program to create novel and useful lines and varieties. Thus, in some embodiments, an $M_1$, $M_2$, $M_3$, or later generation soybean plant containing at least one mutation in a FAD2-1A and at least one mutation in a FAD2-1B gene is crossed with a second soybean plant, and progeny of the cross are identified in which the FAD2-1A and FAD2-1B gene mutations are present. It will be appreciated that the second soybean plant can contain the same FAD2-1A and FAD2-1B mutations as the plant to which it is crossed, different FAD2-1A and FAD2-1B mutations, or be wild-type at the FAD2-1A and/or FAD2-1B loci.

Breeding can be carried out via known procedures. DNA fingerprinting, SNP or similar technologies may be used in a marker-assisted selection (MAS) breeding program to transfer or breed mutant FAD2-1A and FAD2-1B alleles into other soybean plants. For example, a breeder can create segregating populations from hybridizations of a genotype containing a mutant allele with an agronomically desirable genotype. Plants in the $F_2$ or backcross generations can be screened using markers developed from FAD2-1A and FAD2-1B sequences or fragments thereof. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

Successful crosses yield $F_1$ plants that are fertile and that can be backcrossed with one of the parents if desired. In some embodiments, a plant population in the $F_2$ generation is screened for FAD2-1A and FAD2-1B gene expression, e.g., a plant is identified that fails to express FAD2-1A and FAD2-1B due to the absence of a FAD2-1A and FAD2-1B genes according to standard methods, for example, using a PCR method with primers based upon the nucleotide sequence information for FAD2-1A and FAD2-1B described herein. Selected plants are then crossed with one of the parents and the first backcross ($BC_1$) generation plants are self-pollinated to produce a $BC_1F_2$ population that is again screened for variant FAD2-1A and FAD2-1B gene expression (e.g., null versions of the FAD2-1A and FAD2-1B genes). The process of backcrossing, self-pollination, and screening is repeated, for example, at least four times until the final screening produces a plant that is fertile and reasonably similar to the recurrent parent. This plant, if desired, can be self-pollinated, and the progeny subsequently can be screened again to confirm that the plant lacks FAD2-1A and FAD2-1B gene expression. Cytogenetic analyses of the selected plants optionally can be performed to confirm the chromosome complement and chromosome pairing relationships. Breeder's seed of the selected plant can be produced using standard methods including, for example, field testing, confirmation of the null condition for FAD2-1A and FAD2-1B, and/or analyses of oil to determine the level of oleic acid and linoleic acid.

In situations where the original $F_1$ hybrid resulting from the cross between a first, mutant soybean parent and a second, wild-type soybean parent, is hybridized or backcrossed to the mutant soybean parent, the progeny of the backcross can be self-pollinated to create a $BC_1F_2$ generation that is screened for the mutant FAD2-1A and FAD2-1B alleles.

The result of a plant breeding program using the mutant soybean plants described herein can be novel and useful lines and varieties. As used herein, the term "variety" refers to a population of plants that share constant characteristics which separate them from other plants of the same species. A variety is often, although not always, sold commercially. While possessing one or more distinctive traits, a variety can be further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972, on Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A "line" as distinguished from a variety most often denotes a group of plants used non-commercially, for example in plant research. A line typically displays little overall variation between individuals for one or more traits of interest, although there may be some variation between individuals for other traits.

The methods provided herein can be used to produce plant parts (e.g., seeds) or plant products (e.g., oil) having increased oleic acid content and reduced linoleic acid content, as compared corresponding plant parts or products from wild type plants. The fatty acid content of a plant part or a plant product can be evaluated using standard methods, such as those described in Example 5 herein, for example.

The invention will be further described in the following examples, which do not limit the scope of the invention described in the claims.

EXAMPLES

Example 1

Engineering Sequence-specific Nucleases to Mutagenize the FAD2-1A and FAD2-1B Genes To completely inactivate or knock-out the alleles of FAD2-1A and FAD2-1B genes in *G. max*, sequence-specific nucleases were designed that target the protein coding region in the vicinity of the start codon. Eight TAL effector endonuclease pairs were designed to target the FAD2-1 gene family within the first 500 bp of the coding sequence using software that specifically identifies TAL effector endonuclease recognition sites, such as TALE-NT 2.0 (Doyle et al., *Nucleic Acids Res* 40:W117-122, 2012). The TAL effector endonuclease recognition sites for the FAD2-1 genes are underlined in FIG. 1 and are listed in Table 1. TAL effector endonucleases were synthesized using methods similar to those described elsewhere (Cermak et al., *Nucleic Acids Res* 39:e82, 2011; Reyon et al., *Nat Biotechnol* 30:460-465, 2012; and Zhang et al., *Nat Biotechnol* 29:149-153, 2011).

Example 2

FAD2-1 TAL Effector Endonuclease Activity in Yeast

To assess the activity of the TAL effector endonucleases targeting the FAD2-1 genes, activity assays were performed in yeast by methods similar to those described elsewhere (Christian et al., *Genetics* 186:757-761, 2010). For these assays, a target plasmid was constructed with the TAL effector endonuclease recognition site cloned in a non-functional β-galactosidase reporter gene (Table 2). The target site was flanked by a direct repeat of β-galactosidase coding sequence such that if the reporter gene was cleaved by the TAL effector endonuclease, recombination would occur between the direct repeats and function would be restored to the β-galactosidase gene. β-galactosidase activity, therefore, served as a measure of TAL effector endonuclease cleavage activity. Results are summarized in Table 3. All of the FAD2-1 TAL effector endonuclease pairs displayed cleavage activity. Cleavage activities were normalized to the benchmark nuclease, I-SceI.

TABLE 3

FAD2 TAL effector endonuclease activity in yeast

| TAL effector endonuclease subunit | Activity in yeast* | | | |
|---|---|---|---|---|
| | FAD2_T1 | FAD2_T2 | FAD2_T3 | FAD2_T4 |
| FAD2_T01_Left_C11 FAD2_T01_Right_C11 | 0.73 | 0.87 | 0.00 | 0.00 |
| FAD2_T01_Left_C40 FAD2_T01_Right_C40 | 0.79 | 0.73 | 0.00 | 0.00 |
| FAD2_T02_Left_C11 FAD2_T01_Right_C11 | 0.00 | 0.97 | 0.00 | 0.00 |
| FAD2_T02_Left_C40 FAD2_T01_Right_C40 | 0.00 | 0.96 | 0.00 | 0.00 |
| FAD2_T03_Left_C11 FAD2_T03_Right_C11 | 0.00 | 0.00 | 0.65 | 0.53 |
| FAD2_T03_Left_C40 FAD2_T03_Right_C40 | 0.00 | 0.00 | 0.63 | 0.51 |
| FAD2_T04_Left_C11 FAD2_T03_Right_C11 | 0.00 | 0.00 | 0.00 | 0.54 |
| FAD2_T04_Left_C40 FAD2_T03_Right_C40 | 0.00 | 0.00 | 0.00 | 0.52 |

*Normalized to I-SceI (max = 1.0)

TABLE 1

TAL effector endonuclease target sequences

| Gene | Target Sequence Left | SEQ ID NO: | Target Sequence Right | SEQ ID NO |
|---|---|---|---|---|
| FAD2_T01_C11 | GCCACCACCTACTTCCACCTCCT | 18 | ATTGCATGGCCAATCT | 19 |
| FAD2_T01_C40 | GCCACCACCTACTTCCACCTCCT | 20 | ATTGCATGGCCAATCT | 21 |
| FAD2_T02_C11 | ACATTGCCACCACCTACTTCCACCT | 22 | ATTGCATGGCCAATCT | 23 |
| FAD2_T02_C40 | ACATTGCCACCACCTACTTCCACCT | 24 | ATTGCATGGCCAATCT | 25 |
| FAD2_T03_C11 | CTCATGGAAAATAAGCCAT | 26 | ACCGTGATGAAGTGTTTGTCCC | 27 |
| FAD2_T03_C40 | CTCATGGAAAATAAGCCAT | 28 | ACCGTGATGAAGTGTTTGTCCC | 29 |
| FAD2_T04_C11 | ATTTCTCATGGAAAATAAGCCAT | 30 | ACCGTGATGAAGTGTTTGTCCC | 31 |
| FAD2_T04_C40 | ATTTCTCATGGAAAATAAGCCAT | 32 | ACCGTGATGAAGTGTTTGTCCC | 33 |

TABLE 2

FAD2 TAL effector endonuclease Target Sequences for Yeast Assay

| TAL effector endonuclease target | TAL effector endonuclease target sequence | SEQ ID NO: |
|---|---|---|
| FAD2 Target 1 | GCCACCACCTACTTCCACCTCCTTCCTCAACCCTTTTCCCTCATTGCATGGCCAATCT | 34 |
| FAD2 Target 2 | ACATTGCCACCACCTACTTCCACCTCCTTCCTCAACCCTTTTCCCTCATTGCATGGCCAATCT | 35 |
| FAD2 Target 3 | CTCATGGAAAATAAGCCATCGCCGCCATCACTCCAACACAGGTTCCCTTGACCGTGATGAAGTGTTTGTCCC | 36 |
| FAD2 Target 4 | ATTTCTCATGGAAAATAAGCCATCGccgcCATCACTCCAACACAGGTTCCCTTGACCGTGATGAAGTGTTTGTCCC | 7 |

Example 3

TAL Effector Endonuclease Expression and Activity in Soybean Hairy Roots

Based on the activity of the various FAD2 TAL effector endonucleases in yeast, four TAL effector endonucleases in two different scaffolds were chosen for expression in soybean cells (FAD2_T01, FAD2_T02, FAD2_T03 and FAD2_T04). The activities of these TAL effector endonucleases were assessed at their endogenous target sites in soybean using a hairy root assay described elsewhere (Curtin et al. *Plant Physiology* 156(2):466-473, 2011). First, each TAL effector endonuclease was cloned into a T-DNA vector downstream of an estradiol-inducible promoter (Zuo et al., *Plant J.* 24:265-273, 2000), and then transformed into the K599 strain of *Agrobacterium rhizogenes* (Govindarajulu et al., *Mol. Plant Microbe Interact.* 21:1027-1035, 2008). *A. rhizogenes* strains with the various TAL effector endonucleases were then used to infect half-cotyledons of soybean and produce transgenic hairy roots. Three weeks after infection, hairy roots were collected and frozen in liquid nitrogen, and genomic DNA was prepared using standard methods (Murray et al., *Nucl. Acids Res.* 8(19):4321-4325, 1980).

To determine if NHEJ-mediated mutations were created by the TAL effector endonucleases at the target sites in the soybean genome, DNA from nine hairy roots were subjected to a PCR enrichment assay (Zhang et al., *Proc. Natl. Acad. Sci. USA* 107(26):12028-12033, 2010). This assay monitors loss of a restriction enzyme site within the TAL effector endonuclease spacer sequence due to NHEJ-induced mutations. The restriction enzyme sites used in this assay are shown in FIG. 1 (signified by lower case letters). Genomic DNA derived from three hairy root samples expressing FAD2_T01 was digested with MnlI to monitor mutations at the FAD2-1A locus. HphI was used to monitor mutations at FAD2-1B caused by FAD2_T01. AciI was used to monitor mutations at both the FAD2-1A and FAD2-1B loci in digested genomic DNA from six hairy root samples expressing FAD2_T04. Following digestion, an aliquot of each reaction was used as a template for PCR with primers flanking either the FAD2_T01 or FAD2_T04 target sites. To assess activity of FAD2_T01, separate PCR reactions were conducted with primers specific for FAD2-1A and FAD2-1B. PCR products were first analyzed on a 1% agarose gel to verify that amplification had occurred, and then digested with the restriction enzyme located in the spacer sequence of the particular TAL effector endonuclease being analyzed. This second restriction digestion reaction was then analyzed on a 2% agarose gel, along with digested and undigested control DNA from wild type samples. Samples with TAL effector endonuclease-induced NHEJ mutations may lack the restriction enzyme site within the spacer sequence, resulting in an undigested PCR product which appears as a full-length band on the gel. As shown in FIG. 2, undigested PCR products were observed for FAD2-1A, FAD2-1B, or both genes in the same sample. For example, sample "b" in FIG. 2C shows that mutations were present in FAD2-1B, sample "d" in FIG. 2B shows that mutations were present in FAD2-1A, and sample "f" in FIGS. 2B and 2D shows that mutations were present in both FAD2-1A and FAD2-1B.

Undigested PCR products were cloned and sequenced to verify that they contained TAL effector endonuclease-induced mutations in the spacer sequence. The PCR products were cloned using the Qiagen TOPO cloning kit according to manufacturer's instructions. Individual clones derived from a given undigested fragment were sequenced, and the DNA sequences aligned with the wild type FAD2-1A or FAD2-1B sequences. As shown in FIG. 3, multiple, independent deletions were recovered in both FAD2-1A and FAD2-1B, ranging in size from 6 to 92 base pairs.

Example 4

Regeneration of Soybean Plants with TAL Effector Endonuclease-induced Mutations in FAD2 Genes Following verification that FAD2_TAL1 and FAD2_TAL4 created targeted modifications at endogenous target sites, experiments were conducted to create soybean plants with mutations in FAD2-1A and FAD2-1B. To accomplish this, each of the four FAD2-1 TAL effector endonucleases were cloned into a T-DNA vector, and TAL effector endonuclease expression was driven by either the cauliflower mosaic virus 35S promoter or the estradiol-induced XVE promoter system (Zuo et al., supra). The T-DNA vector also contained a bar selectable marker that confers resistance to glufosinate.

Transgenic soybean plants expressing the TAL effector endonucleases were generated using standard *Agrobacterium tumefaciens* transformation protocols (Curtin et al., supra). Following cultivation of the T-DNA-containing *A. tumefaciens* strains with soybean half cotyledons (variety Bert) and subsequent selection for expression of bar, putatively transgenic plants were regenerated. The plants were transferred to soil, and after approximately 4 weeks of growth, a small leaf was harvested from each plant for DNA extraction and genotyping. Each DNA sample was first screened using PCR for the presence of bar. All bar-positive plants were then subjected to a T7E1 assay to identify plants with mutations at the FAD2-1A and FAD2-1B TAL effector endonuclease recognition site (Kim et al., *Genome Res.* 19:1279-1288, 2009). Briefly, a PCR product spanning the TAL effector endonuclease recognition site was generated, denatured, and allowed to reanneal. T7E1 endonuclease was added to the annealed products to cleave heteroduplexes generated when a wild type DNA fragment annealed with a fragment carrying a TAL effector endonuclease-induced mutation, and cleavage products were visualized by agarose gel electrophoresis. As shown in FIG. 4, four plants showed evidence of TAL effector endonuclease-induced mutations (Gm026-18, Gm026-23, Gm027-06 and Gm027-07). In addition, all four plants had mutations at both FAD2-1A and FAD2-1B, indicating that both genes were mutagenized simultaneously. The genotyping data for all plants regenerated is shown in Table 4B.

To determine if mutations introduced by TAL effector endonucleases in leaf tissue were transmitted to the next generation, seeds were collected from T0 plants Gm026-18, Gm026-23 and Gm027-06. In each T1 population, 20-60 individual plants were genotyped to confirm transmission of the mutations. Both FAD2-1A and FAD2-1B mutations segregated in the T1 progeny of GM026-18. In contrast, only FAD2-1A or FAD2-1B mutations were transmitted to the T1 progeny of GM-026-23 and GM027-6, respectively. The DNA sequences of the heritable mutations are shown in FIG. 5.

Example 5

Fatty Acid Profile Analysis on Seeds Produced from TAL Effector Endonuclease-induced Mutations in Soybean FAD2 Genes Seed derived from soybean lines that are homozygous mutant in either FAD2-1A or FAD2-1B, or homozygous for both FAD2-1A and FAD2-1B, are analyzed for fatty acid composition. Briefly, individual soybean seeds derived from Gm026-23, Gm027-6, or Gm026-18 are pulverized individually. DNA is prepared from a portion of the ground tissue and is analyzed to confirm the genotype of each seed. Pulverized tissue from FAD2-1A homozygous (Gm26-23), FAD2-1B homozygous (Gm027-6), or FAD2-1A/FAD2-1B double homozygous (Gm026-18) knock out seeds is pooled. Fatty acid composition is then determined using fatty acid methyl esters (FAME) gas chromatography (Beuselinck et al., *Crop Sci.* 47:747-750, 2006), to assess whether seeds with various FAD2-1 mutations are altered in the proportion of linoleic acid and oleic acid relative to wild type seed.

TABLE 4A

List of regenerated plants and FAD2-1 genes analyzed in FIG. 4

| Lane | DNA | Gene |
|---|---|---|
| 1 | GM026-7a | FADII 1A |
| 2 | GM026-17 | FADII 1A |
| 3 | GM026-18 | FADII 1A |
| 4 | GM026-20 | FADII 1A |
| 5 | GM026-23 | FADII 1A |
| 6 | GM027-3 | FADII 1A |
| 7 | GM027-6 | FADII 1A |
| 8 | GM027-7 | FADII 1A |
| 9 | GM027-10 | FADII 1A |
| 10 | GM027-11 | FADII 1A |
| 11 | GM008-6 | FADII 1A |
| 12 | Bert WT | FADII 1A |
| 13 | GM026-7a | FADII 1A uncut |
| 14 | GM026-17 | FADII 1A uncut |
| 15 | GM026-18 | FADII 1A uncut |
| 16 | GM026-7a | FADII 1B |
| 17 | GM026-17 | FADII 1B |
| 18 | GM026-18 | FADII 1B |
| 19 | GM026-20 | FADII 1B |
| 20 | GM026-23 | FADII 1B |
| 21 | GM027-3 | FADII 1B |
| 22 | GM027-6 | FADII 1B |
| 23 | GM027-7 | FADII 1B |
| 24 | GM027-10 | FADII 1B |
| 25 | GM027-11 | FADII 1B |
| 26 | GM008-6 | FADII 1B |
| 27 | Bert WT | FADII 1B |
| 28 | GM026-7a | FADII 1B uncut |
| 29 | GM026-17 | FADII 1B uncut |
| 30 | GM026-18 | FADII 1B uncut |

TABLE 5

Representative FAD2-1A and FAD2-1B coding sequences*

FAD2-1A

ATGgtcatgatttcactctctctaatctctccattcattttgtagttg
tcattatctttagattttcactacctggtttaaaattgagggattgt
agttctgttggtacatattacacattcagcaaaacaactgaaactcaa
ctgaacttgtttatactttgacacagGGTCTAGCAAAGGAAACAACAA
TGGGAGGTAGAGGTCGTGTGGCCAAAGTGGAAGTTCAAGGGAAGAAGC
CTCTCTCAAGGGTTCCAAACACAAAGCCACCATTCACTGTTGGCCAAC
TCAAGAAAGCAATTCCACCACACTGCTTTCAGCGCTCCCTCCTCACTT
CATTCTCCTATGTTGTTTATGACCTTTCATTTGCCTTCATTTTCTACA
TTGCCACCACCTACTTCCACCTCCTTCCTCAACCCTTTTCCCTCATTG
CATGGCCAATCTATTGGGTTCTCCAAGGTTGCCTTCTCACTGGTGTGT
GGGTGATTGCTCACGAGTGTGGTCACCATGCCTTCAGCAAGTACCAAT
GGGTTGATGATGTTGTGGGTTTGACCCTTCACTCAACACTTTTAGTCC
CTTATTTCTCATGGAAAATAAGCCATCGCCGCCATCACTCCAACACAG
GTTCCCTTGACCGTGATGAAGTGTTTGTCCCAAAACCAAAATCCAAAG
TTGCATGGTTTTCCAAGTACTTAAACAACCCTCTAGGAAGGGCTGTTT
CTCTTCTCGTCACACTCACAATAGGGTGGCCTATGTATTTAGCCTTCA
ATGTCTCTGGTAGACCCTATGATAGTTTTGCAAGCCACTACCACCCTT
ATGCTCCCATATATTCTAACCGTGAGAGGCTTCTGATCTATGTCTCTG
ATGTTGCTTTGTTTTCTGTGACTTACTCTCTCTACCGTGTTGCAACCC
TGAAAGGGTTGGTTTGGCTGCTATGTGTTTATGGGGTGCCTTTGCTCA
TTGTGAACGGTTTTCTTGTGACTATCACATATTTGCAGCACACACACT
TTGCCTTGCCTCATTACGATTCATCAGAATGGGACTGGCTGAAGGGAG
CTTTGGCAACTATGGACAGAGATTATGGGATTCTGAACAAGGTGTTTC
ATCACATAACTGATACTCATGTGGCTCACCATCTCTTCTCTACAATGC
CACATTACCATGCAATGGAGGCAACCAATGCAATCAAGCCAATATTGG
GTGAGTACTACCAATTTGATGACACACCATTTTACAAGGCACTGTGGA
GAGAAGCGAGAGAGTGCCTCTATGTGGAGCCAGATGAAGGAACATCCG
AGAAGGGCGTGTATTGGTACAGGAACAAGTATTGA (SEQ ID NO: 38)

TABLE 4B

Mutant Screening in T0 Transgenic Soybean Plants

| | GM026-7a | GM026-17 | GM026-18 | GM026-20 | GM026-23 | GM027-3 | GM027-6 | GM027-7 | GM027-10 | GM027-11 |
|---|---|---|---|---|---|---|---|---|---|---|
| FAD2-1A | Wt | Wt | Mutation | Wt | Mutation | Wt | Mutation | Mutation | Wt | Wt |
| FAD2-1B | Wt | Wt | Mutation | Wt | Mutation | Wt | Mutation | Mutation | Wt | Wt |

*Wt signifies wild type genotype based on T7E1 assay

TABLE 5-continued

Representative FAD2-1A and FAD2-1B coding sequences*

FAD2-1B

ATGgtcatgatttcactctctataatctgtcacttcctccattcatt ttgtacttctcatatttttcacttcctggttgaaaattgtagttctct tggtacatactagtattagacattcagcaacaacaactgaactgaact tctttatactttgacacagGGTCTAGCAAAGGAAACAATAATGGGAGG

TGGAGGCCGTGTGGCCAAAGTTGAAATTCAGCAGAAGAAGCCTCTCTC

AAGGGTTCCAAACACAAAGCCACCATTCACTGTTGGCCAACTCAAGAA

AGCCATTCCACCGCACTGCTTTCAGCGTTCCCTCCTCACTTCATTGTC

CTATGTTGTTTATGACCTTTCATTGGCTTTCATTTTCTACATTGCCAC

CACCTACTTCCACCTCCTCCCTCACCCCTTTTCCCTCATTGCATGGCC

AATCTATTGGGTTCTCCAAGGTTGCATTCTTACTGGCGTGTGGGTGAT

TGCTCACGAGTGTGGTCACCATGCCTTCAGCAAGTACCCATGGGTTGA

TGATGTTATGGGTTTGACCGTTCACTCAGCACTTTTAGTCCCTTATTT

CTCATGGAAAATAAGCCATCGCCGCCACCACTCCAACACGGGTTCCCT

TGACCGTGATGAAGTGTTTGTCCCAAAACCAAAATCCAAAGTTGCATG

GTACACCAAGTACCTGAACAACCCTCTAGGAAGGGCTGCTTCTCTTCT

CATCACACTCACAATAGGGTGGCCTTTGTATTTAGCCTTCAATGTCTC

TGGCAGACCCTATGATGGTTTTGCTAGCCACTACCACCCTTATGCTCC

CATATATTCAAATCGTGAGAGGCTTTTGATCTATGTCTCTGATGTTGC

TTTGTTTTCTGTGACTTACTTGCTCTACCGTGTTGCAACTATGAAAGG

GTTGGTTTGGCTGCTATGTGTTTATGGGGTGCCATTGCTCATTGTGAA

CGGTTTTCTTGTGACCATCACATATCTGCAGCACACACACTATGCCTT

GCCTCACTATGATTCATCAGAATGGGATTGGCTGAGGGGTGCTTTGGC

AACTATGGACAGAGATTATGGAATTCTGAACAAGGTGTTTCACCACAT

AACTGATACTCATGTGGCTCACCATCTTTTCTCTACAATGCCACATTA

CCATGCAACGGAGGCAACCAATGCAATGAAGCCAATATTGGGTGAGTA

CTACCGATTTGATGACACACCATTTTACAAGGCACTGTGGAGAGAAGC

AAGAGAGTGCCTCTATGTGGAGCCAGATGAAGGAACATCCGAGAAGGG

CGTGTATTGGTACAGGAACAAGTATTGA
(SEQ ID NO: 39)

*intron sequences are in lower case

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A soybean plant, plant part, or plant cell comprising:
   (a) a deletion in each FAD2-1A allele, wherein said deletion in each FAD2-1A allele was induced by transcription activator-like (TAL) effector endonucleases targeted to SEQ ID NOS: 32 and 33, and
   (b) a deletion in each FAD2-1B allele, wherein said deletion in each FAD2-1B allele is 23 bp in size, and wherein said deletion in each FAD2-1B allele was induced by TAL effector endonucleases targeted to SEQ ID NOS: 32 and 33,
   wherein oil produced from said plant, plant part, or plant cell has increased oleic acid content and decreased linoleic acid content as compared to oil produced from a corresponding wild type soybean plant, plant part, or plant cell.

2. The soybean plant, plant part, or plant cell of claim 1, wherein each said FAD2-1A and FAD2-1B allele has a deletion of an endogenous nucleic acid sequence and does not include any exogenous nucleic acid.

3. A soybean plant, plant part, or plant cell comprising:
   (a) a deletion in each FAD2-1A allele, wherein said deletion in each FAD2-1A allele was induced by TAL effector endonucleases targeted to SEQ ID NOS: 32 and 33, and
   (b) a deletion in each FAD2-1B allele, wherein said deletion in each FAD2-1B allele is 23 bp in size, and wherein said deletion in each FAD2-1B allele was induced by TAL effector endonucleases targeted to SEQ ID NOS: 32 and 33,
   wherein oil produced from said plant, plant part, or plant cell has an oleic acid content of greater than 30%.

4. The soybean plant, plant part, or plant cell of claim 3, wherein said oleic acid content is greater than 40%.

5. A soybean plant, plant part, or plant cell comprising:
   (a) a deletion in each FAD2-1A allele, wherein said deletion in each FAD2-1A allele was induced by TAL effector endonucleases targeted to SEQ ID NOS: 32 and 33, and
   (b) a deletion in each FAD2-1B allele, wherein said deletion in each FAD2-1B allele is 23 bp in size, and wherein said deletion in each FAD2-1B allele was induced by TAL effector endonucleases targeted to SEQ ID NOS: 32 and 33,
   wherein oil produced from said plant, plant part, or plant cell has a linoleic acid content of less than 10%.

6. The soybean plant, plant part, or plant cell of claim 5, wherein said linoleic acid content is less than 5%.

7. A method for producing soybean oil having increased oleic acid content and reduced linoleic acid content, comprising:
   (a) providing a soybean plant or plant part comprising
      (i) a deletion in each FAD2-1A allele, wherein said deletion in each FAD2-1A allele was induced by TAL effector endonucleases targeted to SEQ ID NOS: 32 and 33, and
      (ii) a deletion in each FAD2-1B allele, wherein said deletion in each FAD2-1B allele is 23 bp in size, and wherein said deletion in each FAD2-1B allele was induced by TAL effector endonucleases targeted to SEQ ID NOS: 32 and 33; and
   (b) producing oil from said plant or plant part.

8. A method for making a soybean plant comprising a deletion in each FAD2-1A allele and a deletion in each FAD2-1B allele, wherein the deletion in each said FAD2-1B allele is 23 bp in size, said method comprising:
   (a) contacting a population of soybean plant cells comprising functional FAD2-1A and FAD2-1B alleles with a TAL effector endonuclease targeted to SEQ ID NO: 32, and a TAL effector endonuclease targeted to SEQ ID NO: 33,
   (b) selecting, from said population, a cell in which each FAD2-1A allele and each FAD2-1B allele comprises a deletion, wherein said deletion in each FAD2-1A allele was induced by said TAL effector endonucleases targeted to SEQ ID NOS: 32 and 33, wherein said deletion in each FAD2-1B allele was induced by said TAL effector endonucleases targeted to SEQ ID NOS: 32 and 33, and wherein said deletion in each said FAD2-1B allele is 23 bp in size, and (c) regenerating said selected plant cell into a soybean plant.

9. The method of claim 8, wherein said soybean plant cells comprise cotyledon cells, and wherein said methods comprises transforming said cotyledon cells with one or more vectors encoding said TAL effector endonucleases.

10. The method of claim 8, comprising introducing into said plant cells one or more TAL effector endonuclease proteins.

11. The method of claim 8, further comprising culturing said plant cells to generate plant lines.

12. The method of claim 8, further comprising isolating genomic DNA comprising at least a portion of the FAD2-1A locus or at least a portion of the FAD2-1B locus from said plant cells.

13. A method for generating a soybean plant comprising a deletion in each FAD2-1A allele and a deletion in each FAD2-1B allele, wherein the deletion in each said FAD2-1B allele is 23 bp in size, said method comprising:

(a) crossing a first soybean plant comprising a deletion in at least one FAD2-1A allele and a 23 bp deletion in at least one FAD2-1B allele with a second soybean plant comprising a deletion in at least one FAD2-1A allele and a 23 bp deletion in at least one FAD2-1B allele, to obtain progeny, wherein said deletion in at least one FAD2-1A allele in said first soybean plant was induced by TAL effector endonucleases targeted to SEQ ID NOS: 32 and 33, wherein said deletion in at least one FAD2-1B allele in said first soybean plant was induced by TAL effector endonucleases targeted to SEQ ID NOS: 32 and 33, wherein said deletion in at least one FAD2-1A allele in said second soybean plant was induced by TAL effector endonucleases targeted to SEQ ID NOS: 32 and 33, and wherein said deletion in at least one FAD2-1B allele in said second soybean plant was induced by TAL effector endonucleases targeted to SEQ ID NOS: 32 and 33; and (b) from said progeny a soybean plant that comprises a deletion in each FAD2-1A allele and each FAD2-1B allele.

* * * * *

SEQUENCE LISTING

<160> NUMBER OF SEQ ID NOS: 39

<210> SEQ ID NO 1
<211> LENGTH: 289
<212> TYPE: DNA
<213> ORGANISM: Glycine max

<400> SEQUENCE: 1
ttcattttct acattgccac cacctacttc cacctccttc ctcaaccctt tcccctcatt      60
gcatggccaa tctattgggt tctccaaggt tgccttctca ctggtgtgtg ggtgattgct    120
cacgagtgtg gtcaccatgc cttcagcaag taccaatggg ttgatgatgt tgtgggtttg    180
acccttcact caacactttt agtcccttat ttctcatgga aaataagcca tcgccgccat    240
cactccaaca caggttccct tgaccgtgat gaagtgtttg tcccaaaac                289

<210> SEQ ID NO 2
<211> LENGTH: 289
<212> TYPE: DNA
<213> ORGANISM: Glycine max

<400> SEQUENCE: 2
ttcattttct acattgccac cacctacttc cacctcctcc ctcacccctt tcccctcatt      60
gcatggccaa tctattgggt tctccaaggt tgcattctta ctggcgtgtg ggtgattgct    120
cacgagtgtg gtcaccatgc cttcagcaag tacccatggg ttgatgatgt tatgggtttg    180
accgttcact cagcactttt agtcccttat ttctcatgga aaataagcca tcgccgccac    240

```
cactccaaca cgggttccct tgaccgtgat gaagtgtttg tcccaaaac        289
```

<210> SEQ ID NO 3
<211> LENGTH: 76
<212> TYPE: DNA
<213> ORGANISM: Glycine max

<400> SEQUENCE: 3

```
gccaccacct acttccacct ccttcctcaa cccttttccc tcattgcatg gccaatctat    60
tgggttctcc aaggtt                                                    76
```

<210> SEQ ID NO 4
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 4

```
gccaccacct acttccacct ccttcctcaa gattgccaat ctattgggtt ctccaaggtt    60
```

<210> SEQ ID NO 5
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 5

```
gcatggccaa tctattgggt tctccaaggt t                                   31
```

<210> SEQ ID NO 6
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 6

```
gccaccacct acttccacct cctccctcat tgcatggcca atctattggg ttctccaagg    60
tt                                                                   62
```

<210> SEQ ID NO 7
<211> LENGTH: 76
<212> TYPE: DNA
<213> ORGANISM: Glycine max

<400> SEQUENCE: 7

```
atttctcatg gaaataagc catcgccgcc atcactccaa cacaggttcc cttgaccgtg     60
atgaagtgtt tgtccc                                                    76
```

<210> SEQ ID NO 8
<211> LENGTH: 68
<212> TYPE: DNA
<213> ORGANISM: Artificial Sequence
<220> FEATURE:
<223> OTHER INFORMATION: synthetic oligonucleotide

<400> SEQUENCE: 8

```
atttctcatg gaaataagc catcgccgcc atcactccaa cacttgaccg tgatgaagtg     60
tttgtccc                                                             68
```

```
<210> SEQ ID NO 9
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 9
atttctcatg gaaataagc catcgccgcg atgaagtgtt tgtccc            46

<210> SEQ ID NO 10
<211> LENGTH: 70
<212> TYPE: DNA
<213> ORGANISM: Artificial Sequence
<220> FEATURE:
<223> OTHER INFORMATION: synthetic oligonucleotide

<400> SEQUENCE: 10
atttctcatg gaaataagc catcgccgcc accactccaa caccttgac cgtgatgaag    60 tgtttgtccc                                                         70

<210> SEQ ID NO 11
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 11
tgaagtgttt gtccc                                                   15

<210> SEQ ID NO 12
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 12
atttctcatg gaaataaca cgggttccct tgaccgtgat gaagtgtttg tccc          54

<210> SEQ ID NO 13
<211> LENGTH: 77
<212> TYPE: DNA
<213> ORGANISM: Glycine max

<400> SEQUENCE: 13
atttctcatg gaaataagc catcgccgcc atcactccaa cacaggttcc cttgaccgtg    60
atgaagtgtt tgtccca                                                 77

<210> SEQ ID NO 14
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 14
cttgaccgtg atgaagtgtt tgtccca                                      27

<210> SEQ ID NO 15
<211> LENGTH: 77
<212> TYPE: DNA
<213> ORGANISM: Glycine max
```

```
<400> SEQUENCE: 15
atttctcatg gaaaataagc catcgccgcc accactccaa cacgggttcc cttgaccgtg    60
atgaagtgtt tgtccca                                                   77

<210> SEQ ID NO 16
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 16
atttctcatg gaaaataagc catcgccctt gaccgtgatg aagtgtttgt ccca           54

<210> SEQ ID NO 17
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 17
atttctcatg gaaaataagc catcgcctca ggttcccttg accgtgatga agtgtttgtc    60
cca                                                                  63

<210> SEQ ID NO 18
<211> LENGTH: 23
<212> TYPE: DNA
<213> ORGANISM: Glycine max

<400> SEQUENCE: 18
gccaccacct acttccacct cct                                            23

<210> SEQ ID NO 19
<211> LENGTH: 16
<212> TYPE: DNA
<213> ORGANISM: Glycine max

<400> SEQUENCE: 19
attgcatggc caatct                                                    16

<210> SEQ ID NO 20
<211> LENGTH: 23
<212> TYPE: DNA
<213> ORGANISM: Glycine max

<400> SEQUENCE: 20
gccaccacct acttccacct cct                                            23

<210> SEQ ID NO 21
<211> LENGTH: 16
<212> TYPE: DNA
<213> ORGANISM: Glycine max

<400> SEQUENCE: 21
attgcatggc caatct                                                    16

<210> SEQ ID NO 22
<211> LENGTH: 25
<212> TYPE: DNA
<213> ORGANISM: Glycine max
```

```
<400> SEQUENCE: 22
acattgccac cacctacttc cacct                                        25

<210> SEQ ID NO 23
<211> LENGTH: 16
<212> TYPE: DNA
<213> ORGANISM: Glycine max

<400> SEQUENCE: 23
attgcatggc caatct                                                  16

<210> SEQ ID NO 24
<211> LENGTH: 25
<212> TYPE: DNA
<213> ORGANISM: Glycine max

<400> SEQUENCE: 24
acattgccac cacctacttc cacct                                        25

<210> SEQ ID NO 25
<211> LENGTH: 16
<212> TYPE: DNA
<213> ORGANISM: Glycine max

<400> SEQUENCE: 25
attgcatggc caatct                                                  16

<210> SEQ ID NO 26
<211> LENGTH: 19
<212> TYPE: DNA
<213> ORGANISM: Glycine max

<400> SEQUENCE: 26
ctcatggaaa ataagccat                                               19

<210> SEQ ID NO 27
<211> LENGTH: 22
<212> TYPE: DNA
<213> ORGANISM: Glycine max

<400> SEQUENCE: 27
accgtgatga agtgtttgtc cc                                           22

<210> SEQ ID NO 28
<211> LENGTH: 19
<212> TYPE: DNA
<213> ORGANISM: Glycine max

<400> SEQUENCE: 28
ctcatggaaa ataagccat                                               19

<210> SEQ ID NO 29
<211> LENGTH: 22
<212> TYPE: DNA
<213> ORGANISM: Glycine max

<400> SEQUENCE: 29
accgtgatga agtgtttgtc cc                                           22

<210> SEQ ID NO 30
<211> LENGTH: 23
<212> TYPE: DNA
<213> ORGANISM: Glycine max
```

```
<400> SEQUENCE: 30
atttctcatg gaaaataagc cat                                              23

<210> SEQ ID NO 31
<211> LENGTH: 22
<212> TYPE: DNA
<213> ORGANISM: Glycine max

<400> SEQUENCE: 31
accgtgatga agtgtttgtc cc                                               22

<210> SEQ ID NO 32
<211> LENGTH: 23
<212> TYPE: DNA
<213> ORGANISM: Glycine max

<400> SEQUENCE: 32
atttctcatg gaaaataagc cat                                              23

<210> SEQ ID NO 33
<211> LENGTH: 22
<212> TYPE: DNA
<213> ORGANISM: Glycine max

<400> SEQUENCE: 33
accgtgatga agtgtttgtc cc                                               22

<210> SEQ ID NO 34
<211> LENGTH: 58
<212> TYPE: DNA
<213> ORGANISM: Glycine max

<400> SEQUENCE: 34
gccaccacct acttccacct ccttcctcaa ccctttttccc tcattgcatg gccaatct       58

<210> SEQ ID NO 35
<211> LENGTH: 63
<212> TYPE: DNA
<213> ORGANISM: Glycine max

<400> SEQUENCE: 35
acattgccac cacctacttc cacctccttc ctcaacccct ttccctcatt gcatggccaa      60
tct                                                                    63

<210> SEQ ID NO 36
<211> LENGTH: 72
<212> TYPE: DNA
<213> ORGANISM: Glycine max

<400> SEQUENCE: 36
ctcatggaaa ataagccatc gccgccatca ctccaacaca ggttcccttg accgtgatga      60
agtgtttgtc cc                                                          72

<210> SEQ ID NO 37
<211> LENGTH: 9
<212> TYPE: PRT
<213> ORGANISM: Artificial Sequence
<220> FEATURE:
<223> OTHER INFORMATION: consensus

<400> SEQUENCE: 37
```

Leu Ala Gly Leu Ile Asp Ala Asp Gly
1               5

<210> SEQ ID NO 38
<211> LENGTH: 1331
<212> TYPE: DNA
<213> ORGANISM: Glycine max

<400> SEQUENCE: 38

| | | |
|---|---|---|
| atggtcatga tttcactctc tctaatctct ccattcattt tgtagttgtc attatcttta | 60 |
| gattttcac tacctggttt aaaattgagg gattgtagtt ctgttggtac atattacaca | 120 |
| ttcagcaaaa caactgaaac tcaactgaac ttgtttatac tttgacacag ggtctagcaa | 180 |
| aggaaacaac aatgggaggt agaggtcgtg tggccaaagt ggaagttcaa gggaagaagc | 240 |
| ctctctcaag ggttccaaac acaaagccac cattcactgt tggccaactc aagaaagcaa | 300 |
| ttccaccaca ctgctttcag cgctccctcc tcacttcatt ctcctatgtt gtttatgacc | 360 |
| tttcatttgc cttcattttc tacattgcca ccacctactt ccacctcctt cctcaaccct | 420 |
| tttccctcat tgcatggcca atctattggg ttctccaagg ttgccttctc actggtgtgt | 480 |
| gggtgattgc tcacgagtgt ggtcaccatg ccttcagcaa gtaccaatgg gttgatgatg | 540 |
| ttgtgggttt gacccttcac tcaacacttt tagtccctta tttctcatgg aaaataagcc | 600 |
| atcgccgcca tcactccaac acaggttccc ttgaccgtga tgaagtgttt gtcccaaaac | 660 |
| caaaatccaa agttgcatgg ttttccaagt acttaaacaa ccctctagga agggctgttt | 720 |
| ctcttctcgt cacactcaca ataggtggc ctatgtattt agccttcaat gtctctggta | 780 |
| gacccctatga tagttttgca agccactacc acccttatgc tcccatatat tctaaccgtg | 840 |
| agaggcttct gatctatgtc tctgatgttg ctttgttttc tgtgacttac tctctctacc | 900 |
| gtgttgcaac cctgaaaggg ttggtttggc tgctatgtgt ttatggggtg cctttgctca | 960 |
| ttgtgaacgg ttttcttgtg actatcacat atttgcagca cacacacttt gccttgcctc | 1020 |
| attacgattc atcagaatgg gactggctga agggagcttt ggcaactatg acagagatt | 1080 |
| atgggattct gaacaaggtg tttcatcaca taactgatac tcatgtggct caccatctct | 1140 |
| tctctacaat gccacattac catgcaatgg aggcaaccaa tgcaatcaag ccaatattgg | 1200 |
| gtgagtacta ccaatttgat gacacaccat tttacaaggc actgtggaga gaagcgagag | 1260 |
| agtgcctcta tgtggagcca gatgaaggaa catccgagaa gggcgtgtat tggtacagga | 1320 |
| acaagtattg a | 1331 |

<210> SEQ ID NO 39
<211> LENGTH: 1324
<212> TYPE: DNA
<213> ORGANISM: Glycine max

<400> SEQUENCE: 39

| | | |
|---|---|---|
| atggtcatga tttcactctc tctaatctgt cacttccctc cattcatttt gtacttctca | 60 |
| tattttcac ttcctggttg aaaattgtag ttctcttggt acatactagt attagacatt | 120 |
| cagcaacaac aactgaactg aacttcttta ctttgacaca gggtctag caaaggaaac | 180 |
| aataatggga ggtggaggcc gtgtggccaa agttgaaatt cagcagaaga agcctctctc | 240 |
| aagggttcca aacacaaagc caccattcac tgttggccaa ctcaagaaag ccattccacc | 300 |
| gcactgcttt cagcgttccc tcctcacttc attgtcctat gttgtttatg acctttcatt | 360 |
| ggctttcatt ttctacattg ccaccaccta cttccacctc ctccctcacc cttttccct | 420 |

-continued

```
cattgcatgg ccaatctatt gggttctcca aggttgcatt cttactggcg tgtgggtgat    480
tgctcacgag tgtggtcacc atgccttcag caagtaccca tgggttgatg atgttatggg    540
tttgaccgtt cactcagcac ttttagtccc ttatttctca tggaaaataa gccatcgccg    600
ccaccactcc aacacgggtt cccttgaccg tgatgaagtg tttgtcccaa aaccaaaatc    660
caaagttgca tggtacacca agtacctgaa caaccctcta ggaagggctg cttctcttct    720
catcacactc acaatagggt ggcctttgta tttagccttc aatgtctctg gcagacccta    780
tgatggtttt gctagccact accaccctta tgctcccata tattcaaatc gtgagaggct    840
tttgatctat gtctctgatg ttgctttgtt ttctgtgact tacttgctct accgtgttgc    900
aactatgaaa gggttggttt ggctgctatg tgtttatggg gtgccattgc tcattgtgaa    960
cggttttctt gtgaccatca catatctgca gcacacacac tatgccttgc ctcactatga   1020
ttcatcagaa tgggattggc tgaggggtgc tttggcaact atggacagag attatggaat   1080
tctgaacaag gtgtttcacc acataactga tactcatgtg gctcaccatc ttttctctac   1140
aatgccacat taccatgcaa cggaggcaac caatgcaatg aagccaatat tgggtgagta   1200
ctaccgattt gatgacacac cattttacaa ggcactgtgg agagaagcaa gagagtgcct   1260
ctatgtggag ccagatgaag gaacatccga gaagggcgtg tattggtaca ggaacaagta   1320
ttga                                                                1324
```